United States Patent [19]

Bovy et al.

[11] Patent Number: 5,281,615

[45] Date of Patent: * Jan. 25, 1994

[54] CYCLOHEPTIMIDAZOLONE COMPOUNDS AS ANGIOTENSIN II ANTAGONISTS FOR CONTROL OF HYPERTENSION

[75] Inventors: Philippe R. Bovy, St. Louis; Joan M. O'Neal, Glendale; Timothy S. Chamberlain, Chesterfield; Joe T. Collins, Ballwin, all of Mo.

[73] Assignee: G. D. Searle & Co., Skokie, Ill.

[*] Notice: The portion of the term of this patent subsequent to Apr. 14, 2009 has been disclaimed.

[21] Appl. No.: 840,471

[22] Filed: Feb. 24, 1992

Related U.S. Application Data

[63] Continuation of Ser. No. 449,700, Dec. 11, 1989, Pat. No. 5,104,891.

[51] Int. Cl.$^5$ ............... A61K 31/415; C07D 235/02; C07D 257/04
[52] U.S. Cl. ................... 514/381; 514/393; 548/253; 548/302.7
[58] Field of Search .............. 548/323, 253, 302.7; 514/393, 381

[56] References Cited

U.S. PATENT DOCUMENTS

4,816,463  3/1989  Blankley et al. ............ 514/293

FOREIGN PATENT DOCUMENTS

253310     1/1988  European Pat. Off.
43-26504  11/1968  Japan.
65/060069  1/1970  Japan.

OTHER PUBLICATIONS

El-Borai et al. Chem. Abstracts, vol. 108, No. 17; 131673t (1988) and vol. 100; 856314n (1984).
Sunagawa et al. Chem. Abstract vol. 70; 57849h (1969) and vol. 70; 68259s (1969).
P. C. Wong et al, J. Pharmacol. Exp. Ther., 247, (1) 1-7 (1988).
A. T. Chiu et al, European J. Pharmacol., 157, 13-21 (1988).
A. T. Chiu et al, J. Pharmacol. Exp. Ther., 250 (3), 867-874 (1989).
E. F. Godefroi et al, Receuil, 91, 1383-92, (1972).
G. Sunagawa et al, Chem. Pharm. Bull., 16, 1308-15, (1968).
T. Nozoe et al, Bull. Chem. Soc. Japan, 35, 1188, (1962).
M. El Borai et al., Egypt. J. Chem., 28, 139-44 (1985).
M. El Borai et al, J. Prakt. Chem., 325, 853-856 (1983).
M. El Borai et al, OPPI Briefs, 14, 409-414 (1982).

Primary Examiner—Bernard Dentz
Attorney, Agent, or Firm—J. Timothy Keane

[57] ABSTRACT

A class of cycloheptimidazolone compounds is described as angiotensin II antagonists for use in control of hypertension. Compounds of particular interest are those of the formula

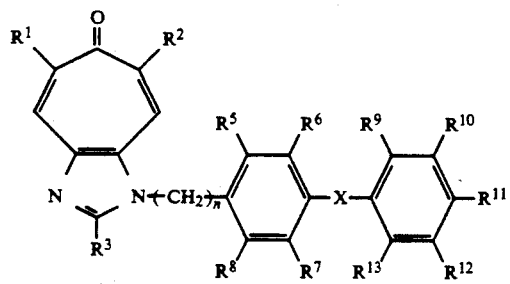

wherein each of $R^1$ and $R^2$ is independently selected from hydrido, alkyl, halo, alkanoyl, carboxyl, alkoxycarbonyl, phenyl, haloalkyl, alkoxyalkyl, formyl, cyano, alkoxy, phenoxy, phenylthio, alkylthio; wherein $R^3$ is alkyl, alkenyl, alkynyl, hydroxyalkyl and alkoxyalkyl; wherein each of $R^5$ through $R^{13}$ is independently selected from hydrido, alkyl, haloalkyl, halo, nitro, cyano, hydroxy, alkoxy, alkylthio, aryl, aryloxy, arythio, and acidic groups such as carboxylic acid, with the proviso that at least one of $R^9$ through $R^{13}$ substituents is an acidic group; or a pharmaceutically-acceptable ester, amide or salt thereof.

21 Claims, No Drawings

CYCLOHEPTIMIDAZOLONE COMPOUNDS AS ANGIOTENSIN II ANTAGONISTS FOR CONTROL OF HYPERTENSION

This is a continuation of application Ser. No. 07/449,700 filed Dec. 11, 1989 now U.S. Pat. No. 5,104,891.

FIELD OF THE INVENTION

A class of non-peptidic angiotensin II antagonist compounds is described herein which are therapeutically useful agents for control of hypertension.

BACKGROUND OF THE INVENTION

The renin-angiotensin system is one of the hormonal mechanisms involved in regulation of pressure/volume homeostasis and expression of hypertension. Activation of the renin-angiotensin cascade begins with renin secretion from the juxtaglomerular apparatus of the kidney and culminates in the formation of angiotensin II, the primary active species of this system. This octapeptide, angiotensin II, is primarily known as a very potent vasoconstrictor agent. It has a number of other effects which include promoting aldosterone secretion, direct effects on the kidney to promote sodium and fluid retention, feedback inhibition of renin secretion, increased sympathetic nervous system activity, increasing vasopressin secretion, causing positive cardiac inotropic effect and modulation of other hormonal systems. Angiotensin II is further degraded to the heptapeptide, angiotensin III {[des Asp$^1$]angiotensin II} by non-specific aminopeptidases. Angiotensin III exhibits a wide range of potency in modulating biological responses upon binding to angiotensin II receptors. For example, angiotensin III is less potent as a vasoconstrictor than angiotensin II, but is similar to angiotensin II in stimulating aldosterone secretion.

A number of amino-, carboxy- and endopeptidases eventually degrade angiotensin III to inactive fragments. Previous studies have shown that antagonizing angiotensin II at its receptors is a viable approach to inhibit the renin-angiotensin system, given the pivotal role of this octapeptide which mediates the actions of the renin-angiotensin system through interaction with various tissue receptors. There are available angiotensin II antagonists most of which are peptidic in nature. Such peptidic compounds are of limited use due to their lack of oral bioavailability and their short duration of action. Also, commercially available peptidic angiotensin II antagonists (e.g., Saralasin) have a significant residual agonist activity which further limit their therapeutical application.

Non-peptidic compounds with angiotensin II antagonist properties are known. For example, the sodium salt of 2-n-butyl-4-chloro-1-(2-chlorobenzyl) imidozoles-s-acetic acid displayed specific competitive angiotensin II antagonist activity in a series of binding experiments, functional assays and in vivo tests [P. C. Wong et al, *J. Pharmacol. Exp. Ther.*, 247, (1) 1-7 (1988)]. The sodium salt of 2-butyl-4-cholor-1-(2-nitrobenzyl)imiadzole-5-acetic acid has specific competitive angiotensin II antagonist activity as shown in a series of binding experiments, functional assays and in vivo test [A. T. Chiu et al, *European J. Pharmacol.*, 157, 3121 (1988)]. A family of 1-benzylimidazole-5-acetate derivatives has been shown to have competitive angiotensin II antagonist properties, [A. T. Chiu et al., *J. Pharmacol. Exp. Ther.*, 250 (3), 867-874]. U.S. Pat. No. 4,816,463 to Blankey et al. describes a family of 4,5,6,7-tetrahydro-1H-imidazo(4,5-C)-tetrahydro-pyridine derivatives useful as antihypertensives, some of which are reported to antagonize the binding of labelled angiotensin II to rat adrenal receptor preparation causing a significant decrease in mean arterial blood pressure in conscious hypertensive rats. E.P. No. 253,310, published Jan. 20, 1988, describes a series of aralkyl imidazole compounds, including in particular a family of biphenyl substituted imidazoles, as antagonists to the angiotensin II receptor.

Several families of cycloheptimidazolone derivatives have been synthesized. For example, the synthesis of 1-benzyl-2-isopropyl-5,7-dimethylimidazo-[4,5-d] cycloheptatrienon-6-one hydrochloride and 1-benzyl-2-isopropyl-5,7-dicarbethoxyimidazo[4,5-d]-cycloheptatrienon-6-one which are characterized by N-1 and C-2 substituants limited to isopropyl and to benzyl, respectively [E. F. Godefroi et al, *Receuil*, 91,1383-92, (1971)]. The compound 2-ethoxy-6(1H)-cycloheptimidazolone has been prepared [G. Senagawa et al, *Chem. Pharm. Bull.*, 16, 1308-15, (1968)]. Synthesis of the compound 2-amino-1-methyl-6(1H)-cyclohepimidazolone has been reported [N. Tatsuo et al, *Bull. Chem. Soc. Japan* 35, 1188 (1962)]. None of these publications mentions any pharmaceutical use.

Several other cycloheptimidazolone derivatives with no substituents on the C-2 position have been reported. For example, a synthesis of a family of 5,7-symmetrically disubstituted-N-methylimidazo[4,5-d]cycloheptatrien-6-one has been reported, including specifically the compound 1,5,7-trimethyl-6(1H)-cycloheptimidazolone [M. El Borai et al., *Egypt. J. Chem.*, 28, 139-44 (1985)]. Also the compound 1,6-dihydro-1-methyl-6-oxo-5,7-cycloimidazoledicarboxylic acid, its methyl and ethyl ester and 1-methyl-6(1H)-cycloheptimidazolone have been synthesized [M. El Borai et al, *J. Prakt. Chem.*, 325, 853-856 (1983)]. Synthesis of the compound 5,7-diphenyl- and 5,7-dichloro-1-methyl-6(1H)-cycloheptimidazolone are also described [M. El Borai et al, *OPPI BRIEFS*, 14, 409-414 (1982)]. None of these compounds is substituted at the C-2 position. None of these publications mentions any pharmaceutical use.

Other types of cycloheptimidazoles are known. For example, Japanese Patent No. 43/26504 of Nov. 14, 1968 describes 2-phenyl-6(1H)-cycloheptimidazolone, 1-methyl-2-phenyl-6(1H)-cycloheptimidazolone and 1-p-tolyl-2-phenyl-6(1H)-cycloheptimidazolone. These compounds, which are characterized by an aryl group at position C-2 and the lack of substituants at positions C-5 and C-7, are for use as desensitizing agents in photographic processes. No mention is made of any pharmaceutical utility.

Japanese Patent No. 65/060069 of Jan. 27, 1970, describes certain cycloheptaimidazole derivatives having antiphlogistic activity.

DESCRIPTION OF THE INVENTION

A class of cycloheptimidazolone compounds useful as angiotensin II antagonists, and which can be used as antihypertensives, is defined by Formula I:

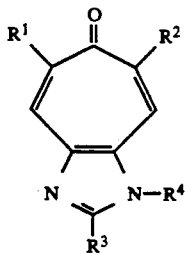 (I)

and the pharmaceutically-acceptable esters, amide and salts thereof; wherein each of $R^1$, $R^2$ and $R^3$ is independently selected from hydrido, linear or branched alkyl, linear or branched alkenyl, linear or branched alkynyl, cycloalkyl, cycloalkenyl, cycloalkylalkyl, cycloalkenylalkyl, aryl, aralkyl, alkylaryl, halo, nitro, cyano, hydroxyl, alkoxy, alkoxyalkyl, aryloxy, alkylthio, alkylsulfinyl, alkylsulphonyl, arylthio, arylsulfinyl, arylsulphonyl and carboxylic acid radicals of the formula

wherein $T^1$ can be hydrido, linear or branched alkyl, linear or branched alkenyl, linear or branched alkynyl, cycloalkyl, cycloalkenyl, cycloalkylalkyl and cycloalkenylalkyl; wherein each of $R^1$, $R^2$ and $R^3$ can be further independently selected from carbonyl radicals of the formula

wherein $T^2$ can be hydrido, linear or branched alkyl, linear or branched alkenyl, linear or branched alkynyl, cycloalkyl, cycloalkenyl, cycloalkylalkyl and cycloalkenylalkyl; and wherein each of $R^1$, $R^2$ and $R^3$ can be further independently selected from carboxamido radicals of the formula

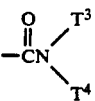

wherein each of $T^3$ and $T^4$ is independently selected from hydrido, linear or branched alkyl, linear or branched alkenyl, linear or branched alkynyl, cycloalkyl, cycloalkenyl, cycloalkylalkyl and cycloalkenylalkyl; wherein $T^3$ and $T^4$ together may form a cyclic structure having five to seven ring atoms, including the nitrogen atom of said carboxamido radical, and having up to a total of three heteroatoms selected from oxygen, nitrogen and sulfur atoms, and wherein said heterocyclic structure may be either saturated or partially unsaturated; wherein each of $R^1$, $R^2$ and $R^3$ is independently selected from an amino group of the formula

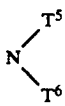

wherein each of $T^5$ and $T^6$ is independently selected from hydrido, linear or branched alkyl, linear or branched alkenyl, linear or branched alkynyl, cycloalkyl, cycloalkenyl, cycloalkylalkyl and cycloalkenylalkyl; wherein $T^5$ and $T^6$ can form together a cyclic structure having five to seven ring atoms, including the nitrogen atom of said amino group, and having up to a total of three heteroatoms selected from oxygen, nitrogen and sulfur atoms, and wherein said heterocyclic structure may be either saturated or partially unsaturated; wherein any one of the foregoing $R^1$, $R^2$, $R^3$ and $T^1$ through $T^6$ substituents having a substitutable position may be substituted with one or more substituents selected from alkyl, haloalkyl, halide, nitro, cyano, aryl, aralkyl, alkylaryl, hydroxyl, alkoxy, aryloxy, alkylthio, alkylsulfinyl, alkylsulphonyl, arylthio, arylsulfinyl and arylsulphonyl; and wherein $R^4$ is a fragment connected to the nitrogen atom at position one of Formula I through a linking group containing at least one linking carbon atom, said $R^4$ fragment selected so that when coupled to the imidazocycloheptimidazolone nucleus of Formula I confers to the thus-formed Formula I compound a functionality with the capacity to be a proton donor in a $pK_a$ range of about one to about ten.

It is understood that, if $R^1$ and $R^2$ have different values from each other, two regioisomers are possible which fall within the scope of the present invention either as individual compounds or as their mixture in all ratios.

A preferred class of substituted cycloheptimidazolones which have angiotensin II properties and can be used as antihypertensives is defined by Formula II:

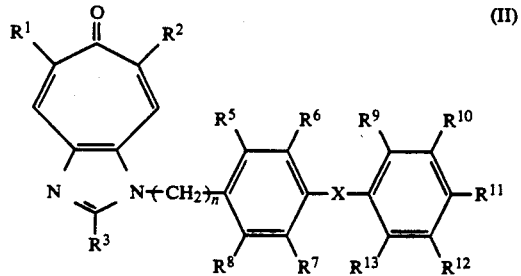 (II)

and the pharmaceutically-acceptable esters, amide and salts thereof; wherein each of $R^1$ and $R^2$ is independently selected from hydrido, linear or branched alkyl, linear or branched alkenyl, linear or branched alkynyl, cycloalkyl, cycloalkenyl, cycloalkylalkyl, cycloalkenylalkyl, aryl, aralkyl, alkylaryl, halo, nitro, cyano, hydroxyl, alkoxy, alkoxyalkyl, aryloxy, alkylthio, alkylsulfinyl, alkylsulphonyl, arylthio, arylsulfinyl, arylsulphonyl and carboxylic acid radicals the formula

wherein T can be hydrido, linear or branched alkyl, linear or branched alkenyl, linear or branched alkynyl, cycloalkyl, cycloalkenyl, cycloalkylalkyl and cycloalkenylalkyl; wherein each of $R^1$ and $R^2$ can be further independently selected from carbonyl radicals of the formula

wherein $T^2$ can be hydrido, linear or branched alkyl, linear or branched alkenyl, linear or branched alkynyl, cycloalkyl, cycloalkenyl, cycloalkylalkyl and cycloalkenylalkyl; and wherein each of $R^1$ and $R^2$ can be further independently selected from a carboxamido radicals of the formula

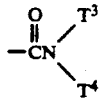

wherein each of $T^3$ and $T^4$ is independently selected from hydrido, linear or branched alkyl, linear or branched alkenyl, linear or branched alkynyl, cycloalkyl, cycloalkenyl, cycloalkylalkyl and cycloalkenylalkyl; wherein each of $T^3$ and $T^4$ together may form a cyclic structure having five to seven ring atoms, including the nitrogen atom of said carboxamido radical, and having up to a total of three heteroatoms selected from oxygen, nitrogen and sulfur atoms, and wherein said heterocyclic structure may be either saturated or partially unsaturated; wherein each of $R^1$ and $R^2$ is independently selected from an amino group of the formula

wherein each of $T^5$ and $T^6$ is independently selected from hydrido, linear or branched alkyl, linear or branched alkenyl, linear or branched alkynyl, cycloalkyl, cycloalkenyl, cycloalkylalkyl and cycloalkenylalkyl; wherein $T^5$ and $T^6$ can form together a cyclic structure having five to seven ring atoms, including the nitrogen atom of said amino group, and having up to a total of three heteroatoms selected from oxygen, nitrogen and sulfur atoms, wherein said heterocyclic structure may be either saturated or partially unsaturated; wherein any one of the foregoing $R^1$ and $R^2$ and $T^1$ through $T^6$ substituents having a substitutable position may be substituted with one or more substituents selected from alkyl, haloalkyl, halide, nitro, cyano, aryl, aralkyl, alkylaryl, hydroxyl, alkoxy, aryloxy, alkylthio, alkylsufinyl, alkylsulphonyl, arylthio arylsulfinyl and arylsulphonyl;

wherein $R^3$ is selected from linear or branched alkyl, alkenyl, alkynyl, alkoxyalkyl, cycloalkyl, cycloalkylalkyl, cycloalkenyl, cycloalkenylalkyl, arylakyl and alkylcycloalkylalkyl, and wherein any one of the foregoing $R^3$ substituents having a substitutable position may be substituted with one or more substituents selected from alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl and arylsulphonyl; wherein n is a number selected from one to about ten, wherein X can be a single bond or be selected from $-O-$, $-S-$, $-CH_2-$, $-CHT^7-$, $-CT^8T^9-$, $-CO-$, $-NH-$, $-NOH-$, $-CH_2-CO-$, $-CO-NH-$, $-CO-NT^{10}-$, $-NH-CO-$ and $-NT^{11}-CO-$; wherein each of $R^5$ to $R^{13}$ is independently one or more groups selected from hydrido, linear or branched alkyl ($C_1-C_{10}$), linear or branched alkenyl ($C_2-C_{10}$), linear or branched alkynyl ($C_2-C_{10}$), cycloalkyl ($C_3-C_{10}$), cycloalkenyl ($C_3-C_{10}$), cycloalkylalkyl ($C_4-C_{10}$), cycloalkenylalkyl ($C_4-C_{10}$), aryl, arylalkyl, alkylaryl, halo, nitro, cyano, hydroxyl, alkoxy, aryloxy, alkylthio, alkylsulfinyl, alkylsulphonyl, arylthio, arylsulfinyl, arylsulphonyl and carboxylic acid radicals of the formula

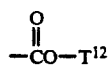

wherein $T^{12}$ can be hydrido, linear or branched alkyl ($C_1-C_{10}$), linear or branched alkenyl ($C_2-C_{10}$), linear or branched alkynyl ($C_2-C_{10}$), cycloalkyl ($C_3-C_{10}$), cycloalkenyl ($C_3-C_{10}$), cycloalkylalkyl ($C_4-C_{10}$) and cycloalkenylalkyl ($C_4-C_{10}$); wherein each of $R^5$ and $R^{13}$ may be further independently selected from carbonyl radicals of the formula

wherein $T^{13}$ can be hydrido, linear or branched alkyl ($C_1-C_{10}$), linear or branched alkenyl ($C_2-C_{10}$), linear or branched alkynyl ($C_2-C_{10}$), cycloalkyl ($C_3-C_{10}$), cycloalkenyl ($C_3-C_{10}$), cycloalkylalkyl ($C_4-C_{10}$) and cycloalkenylalkyl ($C_4-C_{10}$); wherein each of $R^5$ to $R^{13}$ may be further independently selected from carboxamido radicals of the formula

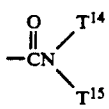

wherein each of $T^{14}$ and $T^{15}$ is independently selected from hydrido, linear or branched alkyl ($C_1-C_{10}$), linear or branched alkenyl ($C_2-C_{10}$), linear or branched alkynyl ($C_2-C_{10}$), cycloalkyl ($C_3-C_{10}$), cycloalkenyl ($C_3-C_{10}$), cycloalkylalkyl ($C_4-C_{10}$) and cycloalkenylalkyl ($C_4-C_{10}$); wherein $T^{14}$ and $T^{15}$ may form together a cyclic structure having five to seven ring atoms, including the nitrogen atom of said carboxamido radical and having up to a total of three heteroatoms selected from oxygen, nitrogen and sulfur atoms and wherein said heterocyclic structure may be either saturated or partially unsaturated; wherein each of $R^5$ to $R^{13}$ may be further independently selected from amino group of the formula

wherein each of $T^{16}$ and $T^{17}$ is independently selected from hydrido, linear or branched alkyl ($C_1-C_{10}$), linear or branched alkenyl ($C_2-C_{10}$), linear or branched alkynyl ($C_2-C_{10}$), cycloalkyl ($C_3-C_{10}$), cycloalkenyl ($C_3-C_{10}$), cycloalkylalkyl ($C_4-C_{10}$) and cycloalkenylalkyl ($C_4-C_{10}$); wherein $T^{16}$ and $T^{17}$ may together form a cyclic structure having four to about nine ring members including the nitrogen atom of the amino group; with the proviso that at least one of the substituents $R^5$ through $R^{13}$ is a free carboxylic acid or is a bioisosteric group to a free carboxylic acid having a $pK_a$ in a range from about two to about ten, said bioisosteric group selected from sulfenic acid, sulfinic acid, sulfonic acid, and phosphorus-containing and thiophosphorus-containing acids selected from

wherein W is selected from O, S and N—$R^{17}$, wherein each of $R^{14}$, $R^{15}$, $R^{16}$ and $R^{17}$ is independently selected from hydrido, alkyl, cycloalkyl, cycloalkylalkyl, haloalkyl, aryl, arylalkyl, hydroxyalkyl, alkoxyalkyl, alkanoyl and $R^{18}$—N—$R^{19}$, wherein $R^{18}$ and $R^{19}$ can be selected from hydrido, alkyl, cycloalkyl, cycloalkylalkyl, haloalkyl, aryl, arylalkyl, hydroxyalkyl, alkoxyalkyl and alkanoyl; wherein said bioisosteric group may be further selected from heterocyclic groups containing five to seven ring members and containing one or more hetero atoms selected from oxygen, nitrogen and sulfur, which heterocyclic group has an ionizable proton with a $pK_a$ in a range from about two to about ten; wherein said bioisosteric group may be further selected from substituted amino groups of the formula

—NH—$R^{20}$ wherein $R^{20}$ is selected from alkylsulfonyl, arylsulfonyl, fluoroalkylsulfonyl, fluoroarylsulfonyl, fluoroalkylcarbonyl and fluoroarylcarbonyl; wherein any one of the foregoing $R^{14}$ through $R^{20}$ and $T^1$ through $T^{17}$ substituents having a subtitutable position may be substituted with one or more substituents independently selected from alkyl, haloalkyl, halo, nitro, cyano, aryl, arylalkyl, alkylaryl, hydroxyl, alkoxy, aryloxy, alkylthio, alkylsulfinyl, alkylsulphonyl, arylthio, arylsulfinyl and arylsulphonyl.

A more preferred class of cycloheptimidazolones which have angiotensin II antagonists properties and can be used as antihypertensives is defined by Formula III:

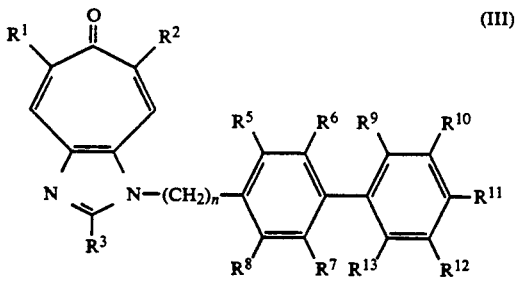

and the pharmaceutically-acceptable esters, amide and salts thereof; wherein each of $R^1$ and $R^2$ is independently selected from hydrido, linear or branched alkyl, linear or branched alkenyl, linear or branched alkynyl, cycloalkyl, cycloalkenyl, cycloalkylalkyl, cycloalkenylalkyl, aryl, aralkyl, alkylaryl, halo, nitro, cyano, hydroxyl, alkoxy, alkoxyalkyl, aryloxy, alkylthio, alkylsulfinyl, alkylsulphonyl, arylthio, arylsulfinyl, arylsulphonyl and carboxylic acid radical of the formula

wherein $T^1$ can be hydrido, linear or branched alkyl, linear or branched alkenyl, linear or branched alkynyl, cycloalkyl, cycloalkenyl, cycloalkylalkyl and cycloalkenylalkyl; wherein each of $R^1$ and $R^2$ can be further independently selected from carbonyl radicals of the formula

wherein $T^2$ can be hydrido, linear or branched alkyl, linear or branched alkenyl, linear or branched alkynyl, cycloalkyl, cycloalkenyl, cycloalkylalkyl and cycloalkenylalkyl; and wherein each of $R^1$ and $R^2$ can be further independently selected from a carboxamido radical of the formula

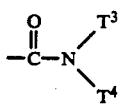

wherein each of $T^3$ and $T^4$ is independently selected from hydrido, linear or branched alkyl, linear or branched alkenyl, linear or branched alkynyl, cycloalkyl, cycloalenyl, cycloalkylalkyl, and cycloalkenylalkyl; wherein $T^3$ and $T^4$ together may form a cyclic structure having five to seven ring atoms, including the nitrogen atom of said carboxamido radical, and having up to a total of three heteroatoms selected from oxygen, nitrogen and sulfur atoms, and wherein said heterocyclic structure may be either saturated or partially unsaturated; wherein $R^1$ and $R^2$ can be an amino group of the formula

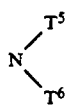

wherein each of $T^5$ and $T^6$ is independently selected from hydrido, linear or branched alkyl, linear or branched alkenyl, linear or branched alkynyl, cycloalkyl, cycloalkenyl, cycloalkylalkyl, and cycloalkenylalkyl; wherein $T^5$ and $T^6$ can form together a cyclic structure having five to seven ring atoms, including the nitrogen atom of said amino group, and having up to a total of three heteroatoms selected from oxygen, nitrogen and sulfur atoms, and wherein said heterocyclic structure may be either saturated or partially unsaturated; wherein any one of the foregoing $R^1$, $R^2$ and $T^1$ through $T^6$ substituents having a substitutable position may be substituted with one or more substituents selected from alkyl, haloalkyl, halide, nitro, cyano, aryl, aralkyl, alkylaryl, hydroxyl, alkoxy, aryloxy, alkylthio, alkylsulfinyl, alkylsulphonyl, arylthio, arylsulfinyl and arylsulphonyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl, and wherein any one of the foregoing $R^3$ substituents having a substitutable position may be substituted with one or more substituents selected from alkyl, haloalkyl, halido, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl and arylsulphonyl; wherein n is a number selected from one to three, inclusive; and each of $R^5$ to $R^{13}$ is independently one or more groups selected from hydrido, alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl, arylsulphonyl carboxylic acid and a bioisosteric group to a free carboxylic acid having a $pK_a$ in a range from about two to about ten selected from sulfenic acid, sulfinic acid, sulfonic acid, phosphorus-containing and thiophosphorus-containing acids selected from

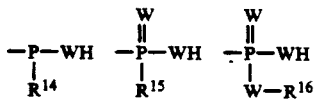

wherein W is selected from O, S and N—$R^{17}$ wherein each of $R^{14}$, $R^{15}$, $R^{16}$ and $R^{17}$ is independently selected from hydrido, alkyl, cycloalkyl, cycloalkylalkyl, haloalkyl, aryl, arylalkyl, hydroxyalkyl, alkoxyalkyl, alkanoyl and $R^{18}$—N-$R^{19}$, wherein $R^{18}$ and $R^{19}$ can be selected from hydrido, alkyl, cycloalkyl, cycloalkylalkyl, haloalkyl, aryl, arylalkyl, hydroxyalkyl, alkoxyalkyl and alkanoyl;

wherein said bioisosteric group may be further selected from heterocyclic groups containing 5 to 7 atoms of which one or more hetero ring atoms are selected from oxygen and nitrogen, which heterocyclic group has an ionizable proton with a $pk_a$ in a range from about two to about ten; wherein said bioisosteric group may be further selected from a substituted amino groups of the formula

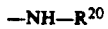

wherein $R^{20}$ is selected from alkylsulfonyl, arylsulfonyl, fluoroalkylsulfonyl, fluoroarylsulfonyl, fluoroalkylcarbonyl and fluoroarylcarbonyl;

wherein any one of the foregoing $R^{14}$ to $R^{20}$ substituents having a substitutable position may be substituted with one or more substituents selected from alkyl, haloalkyl, halide, nitro, cyano, aryl, arylalkyl, alkylaryl, hydroxyl, alkoxy, aryloxy, alkylsulfenyl, alkylthio, alkylsulphonyl, arylsulfenyl, arylthio and arylsulphonyl; with the proviso that at least one of the $R^9$ through $R^{13}$ substituents is said carboxylic acid or said bioisosteric group.

A first highly preferred class of cycloheptimidazolones which have angiotensin II antagonists properties and can be used as antihypertensives is defined by Formula III and the pharmaceutically-acceptable esters, amide and salts thereof; wherein each of $R^1$ and $R^2$ is independently selected from hydrido, linear or branched alkyl linear or branched alkenyl, linear or branched alkynyl, alkoxyalkyl, cycloalkyl, cycloalkenyl, cycloalkylalkyl, cycloalkenylalkyl, aryl, aralkyl and alkylaryl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl, and wherein any one of the foregoing $R^1$, $R^2$ and $R^3$ substituents having a substitutable position may be substituted with one or more substituents selected from alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl and arylsulphonyl; wherein n is a number selected from one to three, inclusive; and each of $R^5$ to $R^8$ is independently one or more groups selected from hydrido, alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl, arylsulphonyl, free carboxylic acid and a bioisosteric group to a free carboxylic acid having a $pK_a$ in a range from about two to about ten selected from sulfenic acid, sulfinic acid, sulfonic acid, phosphorus-containing and thiophosphorus-containing acids selected from

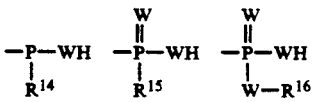

wherein W is selected from O, S and N—$R^{17}$ wherein each of $R^{14}$, $R^{15}$, $R^{16}$ and $R^{17}$ is independently selected from hydrido, alkyl, cycloalkyl, cycloalkylalkyl, haloalkyl, aryl, arylalkyl, hydroxyalkyl, alkoxyalkyl, alkanoyl and $R^{18}$—N—$R^{19}$, wherein $R^{18}$ and $R^{19}$ can be selected from hydrido, alkyl, cycloalkyl, cycloalkylalkyl, haloalkyl, aryl, arylalkyl, hydroxyalkyl, alkoxyalkyl and alkanoyl; wherein said bioisosteric group may be further selected from heterocyclic groups containing 5 to 7 atoms of which one or more hetero ring atoms are selected from oxygen and nitrogen, which heterocyclic group has an ionizable proton with a $pk_a$ in a range from about two to about ten; wherein said bioisosteric group may be further selected from a substituted amino groups of the formula

wherein $R^{20}$ is selected from alkylsulfonyl, arylsulfonyl, fluoroalkylsulfonyl, fluoroarylsulfonyl, fluoroalkylcarbonyl and fluoroarylcarbonyl; wherein any one of the foregoing $R^{14}$ through $R^{20}$ substituents having a substitutable position may be substituted with one or more substituents selected from alkyl, haloalkyl, halo, nitro, cyano, aryl, arylalkyl, alkylaryl, hydroxyl, alkoxy, aryloxy, alkylthio, alkylsulfinyl, alkylsulphonyl, arylsulfenyl, arylthio and arylsulphonyl; with the proviso that at least one of the $R^9$ through $R^{13}$ substituents is said carboxylic acid or said bioisosteric group.

A secondly highly preferred class of cycloheptimidazolones which have angiotensin II antagonists properties and can be used as antihypertensives is defined by Formula III and the pharmaceutically-acceptable esters, amide and salts thereof; wherein each of $R^1$ and $R^2$ is independently selected from hydrido, halo, nitro, cyano, hydroxyl, alkoxy, alkoxyalkyl, aryloxy, alkylthio, alkylsulfinyl, alkylsulphonyl, arylthio, arylsulfinyl and arylsulphonyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl, and wherein any one of the foregoing $R^1$, $R^2$ and $R^3$ substituents having a substitutable position may be substituted with one or more substituents selected from alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl and arylsulphonyl; wherein n is a number selected from one to three, inclusive; wherein each of $R^5$ to $R^8$ is independently one or more groups selected from hydrido, alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl, arylsulphonyl, carboxylic acid and a bioisosteric group to a free carboxylic acid having a $pK_a$ in a range from about two to about ten selected from sulfenic acid, sulfinic acid, sulfonic acid, and phosphorus-containing and thiophosphorus-containing acids selected from

wherein W is selected from O, S and N—$R^{17}$ wherein each of $R^{14}$, $R^{15}$, $R^{16}$ and $R^{17}$ is independently selected from hydrido, alkyl, cycloalkyl, cycloalkylalkyl, haloalkyl, aryl, arylalkyl, hydroxyalkyl, alkoxyalkyl, alkanoyl and $R^{18}$—N—$R^{19}$, wherein $R^{18}$ and $R^{19}$ can be selected from hydrido, alkyl, cycloalkyl, cycloalkylalkyl, haloalkyl, aryl, arylalkyl, hydroxyalkyl, alkoxylalkyl and alkanoyl; wherein said biosteric group may be further selected from heterocyclic groups containing 5 to 7 atoms of which one or more hetero ring atoms are selected from oxygen and nitrogen, which heterocyclic group has an ionizable proton with a $pk_a$ in a range from about two to about ten; wherein said bioisosteric group may be further selected from substituted amino group of the formula

wherein $R^{20}$ is selected from alkylsulfonyl, arylsulfonyl, fluoroalkylsulfonyl, fluoroarylsulfonyl, fluoroalkylcarbonyl and fluoroarylcarbonyl; wherein any one of the foregoing $R^{14}$ through $R^{20}$ substituents having a substitutable position may be substituted with one or more substituents selected from alkyl, haloalkyl, halide, nitro, cyano, aryl, arylalkyl, alkylaryl, hydroxyl, alkoxy, aryloxy, alkylthio, alkylsulfinyl, alkylsulphonyl, arylthio, arylsulfinyl and arylsulphonyl; with the proviso that at least one of the $R^9$ through $R^{13}$ substituents is said carboxylic acid or said bioisosteric group.

A third highly preferred class of cycloheptimidazolones which have angiotensin II antagonists properties and can be used as antihypertensives is defined by Formula III and the pharmaceutically-acceptable esters, amide and salts thereof; wherein each of $R^1$ and $R^2$ is independently selected from hydrido and carboxylic acid radical the formula

wherein $T^1$ can be hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; and wherein any one of the foregoing $T^1$ and $R^3$ substituents having a substitutable position may be substituted with one or more substituents selected from alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl and arylsulphonyl; wherein n is a number selected from one to three, inclusive; wherein each of $R^5$ to $R^8$ is independently one or more groups selected from hydrido, alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl, arylsulphonyl, carboxylic acid and a bioisosteric group to a free carboxylic acid having a $pK_a$ in a range from about two to about ten selected from sulfenic acid, sulfinic acid, sulfonic acid, phosphorus-containing and thiophosphorus-containing acids selected from

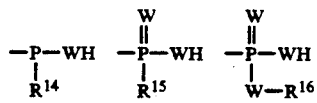

wherein W is selected from O, S and N—$R^{17}$ wherein each of $R^{14}$, $R^{15}$, $R^{16}$ and $R^{17}$ is independently selected from hydrido, alkyl, cycloalkyl, cycloalkylalkyl, haloalkyl, aryl, arylalkyl, hydroxyalkyl, alkoxyalkyl, alkanoyl and $R^{18}$—N—$R^{19}$, wherein $R^{18}$ and $R^{19}$ can be selected from hydrido, alkyl, cycloalkyl, cycloalkylalkyl, haloalkyl, aryl, arylalkyl, hydroxyalkyl, alkoxyalkyl and alkanoyl; wherein said bioisosteric group may be further selected from heterocyclic groups containing 5 to 7 atoms of which one or more hetero ring atoms are selected from oxygen and nitrogen, which heterocyclic group has an ionizable proton with a $pk_a$ in a range from about two to about ten;
wherein said bioisosteric group may be further selected from substituted amino groups of the formula

wherein $R^{20}$ is selected from alkylsulfonyl, arylsulfonyl, fluoroalkylsulfonyl, fluoroarylsulfonyl, fluoroalkylcarbonyl and fluoroarylcarbonyl; wherein any one of the foregoing substituents $R^{14}$ through $R^{20}$ having a substitutable position may be substituted with one or more substituents selected from alkyl, haloalkyl, halide, nitro, cyano, aryl, arylalkyl, alkylaryl, hydroxyl, alkoxy, aryloxy, alkylthio, alkylsulfinyl, alkylsulphonyl, arylthio, arylsulfinyl and arylsulphonyl; with the proviso that at least one of the $R^9$ through $R^{13}$ substituents is said carboxylic acid or said bioisosteric group.

A fourth highly preferred class of cycloheptimidazolones which have angiotensin II antagonists properties and can be used as antihypertensives is defined by Formula III and the pharmaceutically-acceptable esters, amide and salts thereof; wherein each of $R^1$ and $R^2$ can be independently selected from hydrido and carbonyl radicals of the formula

wherein $T^2$ can be hydrido, linear or branched alkyl, linear or branched alkenyl, linear or branched alkynyl, cycloalkyl, cycloalkenyl, cycloalkylalkyl, cycloalkenylalkyl; wherein $R^3$ is selected from linear or branched having suitable positions for substitution may be substituted at any of those positions with one alkyl, alkenyl, alkynyl, alkoxyalkyl, cycloalkyl, cycloalkylalkyl, cycloalkenyl, cycloalkenylalkyl, arylalkyl and alkylcycloalkylalkyl; and wherein any one of the foregoing $T^2$ and $R^3$ substituents having a substitutable position may be substituted with one or more substituents selected from alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl and arylsulphonyl; wherein n is a number selected from one to three, inclusive; and $R^5$ to $R^8$ is independently one or more groups selected from hydrido, alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl, arylsulphonyl, carboxylic acid and a bioisosteric group to a free carboxylic acid having a $pK_a$ in a range from about two to about ten selected from sulfenic acid, sulfinic acid, sulfonic acid, phosphorus-containing and thiophosphorus-containing acids selected from

wherein W is selected from O, S and N—$R^{17}$ wherein each of $R^{14}$, $R^{15}$, $R^{16}$ and $R^{17}$ is independently selected from hydrido, alkyl, cycloalkyl, cycloalkylalkyl, haloalkyl, aryl, arylalkyl, hydroxyalkyl, alkoxyalkyl, alkanoyl and $R^{18}$—N—$R^{19}$, wherein $R^{18}$ and $R^{19}$ can be selected from hydrido, alkyl, cycloalkyl, cycloalkylalkyl, haloalkyl, aryl, arylalkyl, hydroxyalkyl, alkoxyalkyl and alkanoyl; wherein said bioisosteric group may be further selected heterocyclic groups containing 5 to 7 atoms of which one or more hetero ring atoms are selected from oxygen and nitrogen, which heterocyclic group has an ionizable proton with a $pk_a$ in a range from about two to about ten; wherein said bioisosteric groups may be further selected from substituted amino group of the formula

wherein $R^{20}$ is selected from alkylsulfonyl, arylsulfonyl, fluoroalkylsulfonyl, fluoroarylsulfonyl, fluoroalkylcarbonyl and fluoroarylcarbonyl; wherein any one of the foregoing substituents $R^{14}$ through $R^{20}$ having a substitutable position may be substituted with one or more substituents selected from alkyl, haloalkyl, halo, nitro, cyano, aryl, arylalkyl, alkylaryl, hydroxyl, alkoxy, aryloxy, alkylsulfenyl, alkylsulfinyl, alkylsulphonyl, arylsulfenyl, arylsulfinyl and arylsulphonyl; with the proviso that at least one of the $R^9$ through $R^{13}$ substituents is said carboxylic acid or said bioisosteric group.

A fifth highly preferred class of cycloheptimidazolones which have angiotensin II antagonists properties and can be used as antihypertensives is defined by Formula III and the pharmaceutically-acceptable esters, amide and salts thereof; wherein each of $R^1$ and $R^2$ can be independently selected from hydrido and carboxamido radical of the formula

wherein each of $T^3$ and $T^4$ is independently selected from hydrido, linear or branched alkyl, linear or branched alkenyl, linear or branched alkynyl, cycloalkyl, cycloalkenyl, cycloalkylalkyl and cycloalkenylalkyl; wherein $T^3$ and $T^4$ together may form a cyclic structure having five to seven ring atoms, including the nitrogen atom of said carboxamido radical, and having up to a total of three heteroatoms selected from oxygen, nitrogen and sulfur atoms, and wherein said heterocyclic structure may be either saturated or partially unsaturated; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; and wherein any one of the foregoing $T^3$, $T^4$ and $R^3$ substituents having a substitutable position may be substituted with one or more substituents selected from alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl and arylsulphonyl; wherein n is a number selected from one to three, inclusive; wherein each of $R^5$ to $R^8$ is independently one or more groups selected from hydrido, alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl, arylsulphonyl, carboxylic acid or a bioisosteric group to a free carboxylic acid having a $pK_a$ in a range from about two to about ten selected from sulfenic acid, sulfinic acid, sulfonic acid, phosphorus-containing and thiophosphorus-containing acids selected from

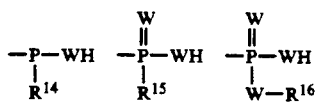

wherein W is selected from O, S and N—$R^{17}$ wherein each of $R^{14}$, $R^{15}$, $R^{16}$ and $R^{17}$ is independently selected from hydrido, alkyl, cycloalkyl, cycloalkylalkyl, haloalkyl, aryl, arylalkyl, hydroxyalkyl, alkoxyalkyl, alkanoyl and $R^{18}$—N—$R^{19}$, wherein $R^{18}$ and $R^{19}$ can be selected from hydrido, alkyl, cycloalkyl, cycloalkylalkyl, haloalkyl, aryl, arylalkyl, hydroxyalkyl, alkoxyalkyl and alkanoyl; wherein said bioisosteric group is further selected from heterocyclic groups containing 5 to 7 atoms of which one or more hetero ring atoms are selected from oxygen and nitrogen, which heterocyclic group has an ionizable proton with a $pk_a$ in a range from about two to about ten; wherein said bioisosteric group is further substituted amino groups of the formula

wherein $R^{20}$ is selected from alkylsulfonyl, arylsulfonyl, fluoroalkylsulfonyl, fluoroarylsulfonyl, fluoroalkylcarbonyl and fluoroarylcarbonyl; wherein any one of the foregoing $R^{14}$ through $R^{20}$ substituents having a substitutable position may be substituted with one or more substituents selected from alkyl, haloalkyl, halide, nitro, cyano, aryl, arylalkyl, alkylaryl, hydroxyl, alkoxy, aryloxy, alkylthio, alkylsulfinyl, alkylsulphonyl, arylsulthio, arylsulfinyl and arylsulphonyl; with the proviso that at least one of the $R^9$ through $R^{13}$ substituents is said carboxylic acid or said bioisosteric group.

A sixth highly preferred class of cycloheptimidazolones which have angiotensin II antagonists properties and can be used as antihypertensives is defined by Formula III and the pharmaceutically-acceptable esters, amide and salts thereof; wherein each of $R^1$ and $R^2$ may be independently selected from hydrido and an amino groups of the formula

wherein each of $T^5$ and $T^6$ is independently selected from hydrido, linear or branched alkyl, linear or branched alkenyl, linear or branched alkynyl, cycloalkyl, cycloalkenyl, cycloalkylalkyl and cycloalkenylalkyl; wherein $T^5$ and $T^6$ can form together a cyclic structure having five to seven ring atoms, including the nitrogen atom of said amino group, and having up to a total of three heteroatoms selected from oxygen, nitrogen and sulfur atoms, and wherein said heterocyclic structure may be either saturated or partially unsaturated; wherein any one of the foregoing $T^5$ and $T^6$ substituents having a substitutable position may be substituted with one or more substituents selected from alkyl, haloalkyl, halo, nitro, cyano, aryl, aralkyl, alkylaryl, hydroxyl, alkoxy, aryloxy, alkylthio, alkylsulfinyl, alkylsulphonyl, arylthio, arylsulfinyl and arylsulphonyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl, and wherein any one of the foregoing $R^3$ substituent having a substitutable position may be substituted with one or more substituents selected from alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl and arylsulphonyl; wherein n is a number selected from one to three, inclusive; wherein each of $R^5$ to $R^8$ is independently one or more groups selected from hydrido, alkyl, haloalkyl, halo, nitro, cyano, aryl, arylamino, alkylamino, alkylarylamino, hydroxyl, alkoxy, aryloxy, alkylthio, alkylsulfinyl, alkylsulphonyl, arylthio, arylsulfinyl, arylsulphonyl, carboxylic acid or a bioisosteric group to a free carboxylic acid having a $pK_a$ in a range from about two to about ten selected from sulfenic acid, sulfinic acid, sulfonic acid, phosphorus-containing and thiophosphorus-containing acids selected from

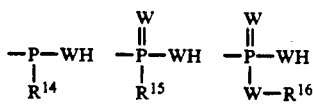

wherein W is selected from O, S and N—$R^{17}$ wherein each of $R^{14}$, $R^{15}$ and $R^{16}$ is independantly selected from hydrido, alkyl, cycloalkyl, cycloalkylalkyl, haloalkyl, aryl, arylalkyl, hydroxyalkyl, alkoxyalkyl, alkanoyl and $R^{18}$—N—$R^{19}$, wherein $R^{18}$ and $R^{19}$ can be selected from hydrido, alkyl, alkyl, cycloalkyl, cycloalkylalkyl, haloalkyl, aryl, arylalkyl, hydroxyalkyl, alkoxyalkyl and alkanoyl; wherein said bioisosteric group may be further selected from heterocyclic groups containing 5 to 7 atoms of which one or more heterocyclic ring atoms are selected from oxygen and nitrogen, which heterocyclic group has an ionizable proton with a $pk_a$ in a range from about two to about ten; wherein said bioisosteric group may be further selected from substituted amino groups of the formula

wherein $R^{20}$ is selected from alkylsulfonyl, arylsulfonyl, fluoroalkylsulfonyl, fluoroarylsulfonyl, fluoroalkylcarbonyl and fluoroarylcarbonyl; wherein any one of the foregoing substituents $R^{14}$ through $R^{20}$ having a substitutable position may be substituted with one or more substituents selected from alkyl, haloalkyl, halo, nitro, cyano, aryl, arylalkyl, alkylaryl, hydroxyl, alkoxy, aryloxy, alkylthio, alkylsulfinyl, alkylsulphonyl, arylthio, arylsulfinyl and arylsulphonyl; with the proviso that at least one of the $R^9$ through $R^{13}$ substituents is said carboxylic acid or said bioisosteric group.

The term "hydrido" denotes a single hydrogen atom (H) which may be attached, for example, to a carbon atom or attached to an oxygen atom to form an hydroxyl group. Where the term "alkyl" is used, either alone or within other terms such as "haloalkyl" and "hydroxyalkyl", the term "alkyl" embraces linear atoms or, preferably, one to about ten carbon atoms. More preferred alkyl radicals are "lower alkyl" radicals having one to about five carbon atoms. The term "cycloalkyl" embraces cyclic radicals having three to about ten ring carbon atoms, preferably three to about six carbon atoms, such as cyclopropyl and cyclobutyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are trifluoromethyl, 2,2,2-trifluoroethyl, perfluoroethyl and 2,2,3,3-tetrafluoropropyl groups. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond. The term "alkynyl" embraces linear or branched radicals having two to about twenty carbon atoms, preferably two to about ten carbon atoms, and containing at least one carbon-carbon triple bond. The terms "cycloalkenyl"0 and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals each having alkyl portions of one to about ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methylthio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals >SO and >SO$_2$. The term "acyl" whether used alone, or within a term such as acyloxy, denotes a radical provided by the residue after removal of hydroxyl from an organic acid, examples of such radical being acetyl and benzoyl. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Examples of acidic bioisosteres of carboxylic acid are the following: sulfonic acid, alkyl phosphinous acid, phosphonic acid, alkyl phosphite, phosphate, alkylphosphate, hydroxamic acid, phenylsulphonamide, methylsulphonamide, trifluoromethylsulfonamide, N-cyanoamide and N-trifluoroacetyl-amine. Examples of acidic bioisosteres provided by heterocylic 5- or 6-membered rings, which may also be fused to one or both rings of a biphenyl moiety and which contain one or several heteroatoms and having an ionizable proton in a pK$_a$ range of about two to about ten, are as follows:

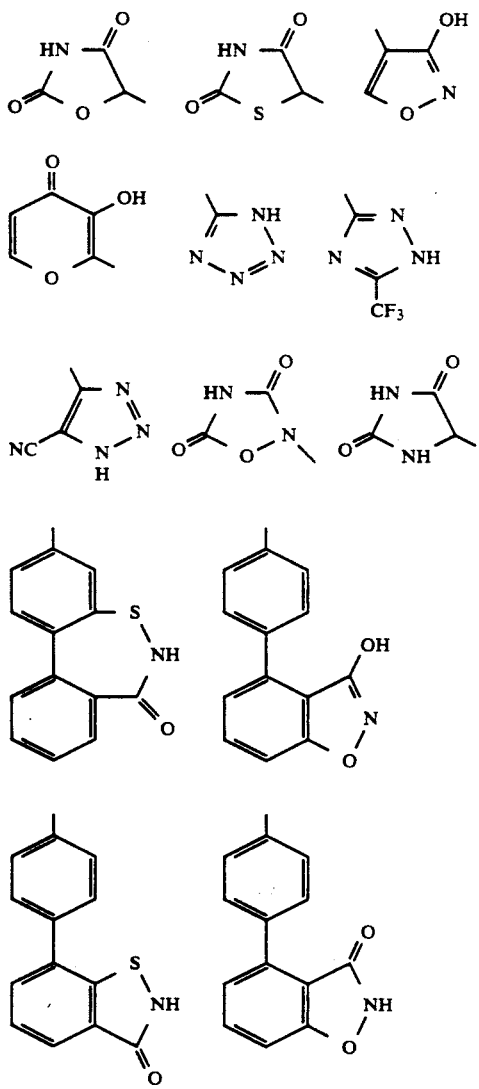

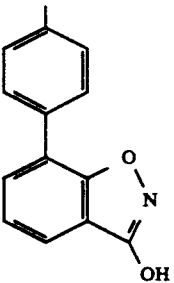

Specific examples of alkyl groups are methyl, ethyl, n-propyl, isopropyl, n-butyl, sec-butyl, iso-butyl, tert-butyl, n-pentyl, iso-pentyl, methylbutyl, dimethylbutyl and neopentyl. Typical alkenyl and alkynyl groups may have one unsaturated bond, such as an allyl group, or may have a plurality or unsaturated bonds, with such plurality of bonds either adjacent, such as allene-type structures, or in conjugation, or separated by several saturated carbons.

Compounds of Formula I have been found to inhibit angiotensin II in mammals. Angiotensin II is a potent vasoconstrictor and participates in the formation of aldosterone which regulates sodium and water balance in mammals. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from the effects of hypertension or susceptible to a hypertensive condition if not treated to prevent or control such hypertension.

Included within the family of compounds of Formulas I-III are the tautomeric forms of the described compounds, isomeric forms including diastereoisomers, and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Specific compounds of the invention of interest are the following:

4'-[[2-butyl-6(1H)-cycloheptimidazolon-1-yl]methyl]-[1,1'-biphenyl]-2-carboxylic acid;
4'-[[5,7-dimethyl-2-butyl-6(1H)-cycloheptimidazolon-1-yl]methyl]-[1,1'-biphenyl]-2-carboxylic acid;
4'-[[5,7-diethyl-2-butyl-6(1H)-cycloheptimidazolon-1-yl]methyl]-[1,1'-biphenyl]-2-carboxylic acid;
4'-[[5,7-dipropyl-2-butyl-6(1H)-cycloheptimidazolon-1-yl]methyl]-[1,1'-biphenyl]-2-carboxylic acid;
4'-[[5,7-dibutyl-2-butyl-6(1H)-cycloheptimidazolon-1-yl]methyl]-[1,1'-biphenyl]-2-carboxylic acid;
4'-[[5,7-dipentyl-2-butyl-6(1H)-cycloheptimidazolon-1-yl]methyl]-[1,1'-biphenyl]-2-carboxylic acid;
4'-[[5,7-dihexyl-2-butyl-6(1H)-cycloheptimidazolon-1-yl]methyl]-[1,1'-biphenyl]-2-carboxylic acid;
4'-[[5,7-diheptyl-2-butyl-6(1H)-cycloheptimidazolon-1-yl]methyl]-[1,1'-biphenyl]-2-carboxylic acid;
4'-[[5,7-dioctyl-2-butyl-6(1H)-cycloheptimidazolon-1-yl]methyl]-[1,1'-biphenyl]-2-carboxylic acid;
4'-[[5,7-dinonyl-2-butyl-6(1H)-cycloheptimidazolon-1-yl]methyl]-[1,1'-biphenyl]-2-carboxylic acid;
4'-[[5,7-didecyl-2-butyl-6(1H)-cycloheptimidazolon-1-yl]methyl]-[1,1'-biphenyl]-2-carboxylic acid;
4'-[[2-propyl-6(1H)-cycloheptimidazolon-1-yl]methyl]-[1,1'-biphenyl]-2-carboxylic acid;
4'-[[5,7-dimethyl-2-propyl-6(1H)-cycloheptimidazolon-1-yl]methyl]-[1,1'-biphenyl]-2-carboxylic acid;
4'-[[5,7-diethyl-2-propyl-6(1H)-cycloheptimidazolon-1-yl]methyl]-[1,1'-biphenyl]-2-carboxylic acid;
4'-[[5,7-dipropyl-2-propyl-6(1H)-cycloheptimidazolon-1-yl]methyl]-[1,1'-biphenyl]-2-carboxylic acid;
4'-[[5,7-dibutyl-2-propyl-6(1H)-cycloheptimidazolon-1-yl]methyl]-[1,1'-biphenyl]-2-carboxylic acid;
4'-[[5,7-dipentyl-2-propyl-6(1H)-cycloheptimidazolon-1-yl]methyl]-[1,1'-biphenyl]-2-carboxylic acid;
4'-[[5,7-dihexyl-2-propyl-6(1H)-cycloheptimidazolon-1-yl]methyl]-[1,1'-biphenyl]-2-carboxylic acid;
4'-[[5,7-diheptyl-2-propyl-6(1H-cycloheptimidazolon-1-yl]methyl]-[1,1'-biphenyl]-2-carboxylic acid;
4'-[[5,7-dioctyl-2-propyl-6(1H)-cycloheptimidazolon-1-yl]methyl]-[1,1'-biphenyl]-2-carboxylic acid;
4'-[[5,7-dinonyl-2-propyl-6(1H)-cycloheptimidazolon-1-yl]methyl]-[1,1'-biphenyl]-2-carboxylic acid;
4'-[[5,7-didecyl-2-propyl-6(1H)-cycloheptimidazolon-1-yl]methyl]-[1,1'-biphenyl]-2-carboxylic acid;
4'-[[2-pentyl-6(1H)-cycloheptimidazolon-1-yl]methyl]-[1,1'-biphenyl]-2-carboxylic acid;
4'-[[5,7-dimethyl-2-pentyl-6(1H)-cycloheptimidazolon-1-yl]methyl]-[1,1'-biphenyl]-2-carboxylic acid;
4'-[[5,7-diethyl-2-pentyl-6(1H)-cycloheptimidazolon-1-yl]methyl]-[1,1'-biphenyl]-2-carboxylic acid;
4'-[[5,7-dipropyl-2-pentyl-6(1H)-cycloheptimidazolon-1-yl]methyl]-[1,1'-biphenyl]-2-carboxylic acid;
4'-[[5,7-dibutyl-2-pentyl-6(1H)-cycloheptimidazolon-1-yl]methyl]-[1,1'-biphenyl]-2-carboxylic acid;
4'-[[5,7-dipentyl-2-pentyl-6(1H)-cycloheptimidazolon-1-yl]methyl]-[1,1'-biphenyl]-2-carboxylic acid;
4'-[[5,7-dihexyl-2-pentyl-6(1H)-cycloheptimidazolon-1-yl]methyl]-[1,1'-biphenyl]-2-carboxylic acid;
4'-[[5,7-diheptyl-2-pentyl-6(1H)-cycloheptimidazolon-1-yl]methyl]-[1,1'-biphenyl]-2-carboxylic acid;
4'-[[5,7-dioctyl-2-pentyl-6(1H)-cycloheptimidazolon-1-yl]methyl]-[1,1'-biphenyl]-2-carboxylic acid;
4'-[[5,7-dinonyl-2-pentyl-6(1H)-cycloheptimidazolon-1-yl]methyl]-[1,1'-biphenyl]-2-carboxylic acid;
4'-[[5,7-didecyl-2-pentyl-6(1H)-cycloheptimidazolon-1-yl]methyl]-[1,1'-biphenyl]-2-carboxylic acid;
4'-[[2-hexyl-6(1H)-cycloheptimidazolon-1-yl]methyl]-[1,1'-biphenyl]-2-carboxylic acid;
4'-[[5,7-dimethyl-2-hexyl-6(1H)-cycloheptimidazolon-1-yl]methyl]-[1,1'-biphenyl]-2-carboxylic acid;
4'-[[5,7-diethyl-2-hexyl-6(1H)-cycloheptimidazolon-1-yl]methyl]-[1,1'-biphenyl]-2-carboxylic acid;
4'-[[5,7-dipropyl-2-hexyl-6(1H)-cycloheptimidazolon-1-yl]methyl]-[1,1'-biphenyl]-2-carboxylic acid;
4'-[[5,7-dibutyl-2-hexyl-6(1H)-cycloheptimidazolon-1-yl]methyl]-[1,1'-biphenyl]-2-carboxylic acid;
4'-[[5,7-dipentyl-2-hexyl-6(1H)-cycloheptimidazolon-1-yl]methyl]-[1,1'-biphenyl]-2-carboxylic acid;
4'-[[5,7-dihexyl-2-hexyl-6(1H)-cycloheptimidazolon-1-yl]methyl]-[1,1'-biphenyl]-2-carboxylic acid;
4'-[[5,7-diheptyl-2-hexyl-6(1H)-cycloheptimidazolon-1-yl]methyl]-[1,1'-biphenyl]-2-carboxylic acid;
4'-[[5,7-dioctyl-2-hexyl-6(1H)-cycloheptimidazolon-1-yl]methyl]-[1,1'-biphenyl]-2-carboxylic acid;
4'-[[5,7-dinonyl-2-hexyl-6(1H)-cycloheptimidazolon-1-yl]methyl]-[1,1'-biphenyl]-2-carboxylic acid;
4'-[[5,7-didecyl-2-hexyl-6(1H)-cycloheptimidazolon-1-yl]methyl]-[1,1'-biphenyl]-2-carboxylic acid;
4'-[[5,7-difluoro-2-butyl-6(1H)-cycloheptimidazolon-1-yl]methyl]-[1,1'-biphenyl]-2-carboxylic acid;
4'-[[5,7-dichloro-2-butyl-6(1H)-cycloheptimidazolon-1-yl]methyl]-[1,1'-biphenyl]-2-carboxylic acid;
4'-[[5,7-dibromo-2-butyl-6(1H)-cycloheptimidazolon-1-yl]methyl]-[1,1'-biphenyl]-2-carboxylic acid;
4'-[[5,7-diiodo-2-butyl-6(1H)-cycloheptimidazolon-1-yl]methyl]-[1,1'-biphenyl]-2-carboxylic acid;
4'-[[5,7-dihydroxy-2-butyl-6(1H)-cycloheptimidazolon-1-yl]methyl]-[1,1'-biphenyl]-2-carboxylic acid;
4'-[[5,7-dimethoxy-2-butyl-6(1H)-cycloheptimidazolon-1-yl]methyl]-[1,1'-biphenyl]-2-carboxylic acid;
4'-[[5,7-dipropoxy-2-butyl-6(1H)-cycloheptimidazolon-1-yl]methyl]-[1,1'-biphenyl]-2-carboxylic acid;
4'-[[5,7-diphenoxy-2-butyl-6(1H)-cycloheptimidazolon-1-yl]methyl]-[1,1'-biphenyl]-2-carboxylic acid;
4'-[[5,7-dithiomethyl-2-butyl-6(1H)-cycloheptimidazolon-1-yl]methyl]-[1,1'-biphenyl]-2-carboxylic acid;
4'-[[5,7-dithiophenyl-2-butyl-6(1H)-cycloheptimidazolon-1-yl]methyl]-[1,1'-biphenyl]-2-carboxylic acid;
4'-[[5,7-dicyano-2-butyl-6(1H)-cycloheptimidazolon-1-yl]methyl]-[1,1'-biphenyl]-2-carboxylic acid;
4'-[[5,7-dinitro-2-butyl-6(1H)-cycloheptimidazolon-1-yl]methyl]-[1,1'-biphenyl]-2-carboxylic acid;
4'-[[5,7-diphenyl-2-butyl-6(1H)-cycloheptimidazolon-1-yl]methyl]-[1,1'-biphenyl]-2-carboxylic acid;
4'-[[5,7-diformyl-2-butyl-6(1H)-cycloheptimidazolon-1-yl]methyl]-[1,1'-biphenyl]-2-carboxylic acid;
4'-[[5-hydroxy-7-chloro-2-butyl-6(1H)-cycloheptimidazolon-1-yl]methyl]-[1,1'-biphenyl]-2-carboxylic acid;
4'-[[5-chloro-7-hydroxy-2-butyl-6(1H)-cycloheptimidazolon-1-yl]methyl]-[1,1'-biphenyl]-2-carboxylic acid;
4'-[[5-carboxylic acid-7-methoxymethyl-2-butyl-6(1H)-cycloheptimidazolon-1-yl]methyl]-[1,1'-biphenyl]-2-carboxylic acid;
4'-[[5-methoxymethyl-7-carboxylic acid-2-butyl-6(1H)-cycloheptimidazolon-1-yl]methyl]-[1,1'-biphenyl]-2-carboxylic acid;

4'-[[5,7-dicarboxylic acid-2-butyl-6(1H)-cycloheptimidazolon-1-yl]methyl]-[1,1'-biphenyl]-2-carboxylic acid;

4'-[[5,7-dimethoxycarbonyl-2-butyl-6(1H)-cycloheptimidazolon-1-yl]methyl]-[1,1'-biphenyl]-2-carboxylic acid;

4'-[[5,7-diethoxycarbonyl-2-butyl-6(1H)-cycloheptimidazolon-1-yl]methyl]-[1,1'-biphenyl]-2-carboxylic acid;

4'-[[5,7-dibenzyloxycabonyl-2-butyl-6(1H)-cycloheptimidazolon-1-yl]methyl]-[1,1'-biphenyl]-2-carboxylic acid;

4'-[[5,7-dicarboxamide-2-butyl-6(1H)-cycloheptimidazolon-1-yl]methyl]-[1,1'-biphenyl]-2-carboxylic acid;

4'-[[5,7-di-N-methylcarboxamide-2-butyl-6(1H)-cycloheptimidazolon-1-yl]methyl]-[1,1'-biphenyl]-2-carboxylic acid;

4'-[[5,7-di-N-ethylcarboxamide-2-butyl-6(1H)-cycloheptimidazolon-1-yl]methyl]-[1,1'-biphenyl]-2-carboxylic acid;

4'-[[5,7-dibenzoyl-2-butyl-6(1H)-cycloheptimidazolon-1-yl]methyl]-[1,1'-biphenyl]-2-carboxylic acid;

4'-[[5(7)-isopropyl-7(5)phenyl-2-butyl-6(1H)-cycloheptimidazolon-1-yl]-methyl]-[1,1'-biphenyl]-2-carboxylic acid;

4'-[[5(7)-hydroxy-7(5)chloro-2-butyl-6(1H)-cycloheptimidazolon-1-yl]-methyl]-[1,1'-biphenyl]-2-carboxylic acid;

4'-[[5(7)-carboxy-7(5)methoxymethyl-2-butyl-6(1H)-cycloheptimidazolon-1-yl]methyl]-[1,1'-biphenyl]-2-carboxylic acid;

4'-[[5(7)-hydrido-7(5)benzyl-2-propyl-6(1H)-cycloheptimidazolon-1-yl]-methyl]-[1,1'-biphenyl]-2-carboxylic acid;

4'-[[5(7)-benzyl-7(5)hydrido-2-butyl-6(1H)-cycloheptimidazolon-1-yl]-methyl]-[1,1'-biphenyl]-2-carboxylic acid;

4'-[[5,7-dimethyl-2-butyl-6(1H)-cycloheptimidazolon-1-yl]methyl]-[1,1'-biphenyl]-2-carboxylic acid, methyl ester;

4'-[[5,7-diethoxycarbonyl-2-butyl-6(1H)-cycloheptimidazolon-1-yl]methyl]-[1,1'-biphenyl]-2-carboxylic acid, ethyl ester;

4'-[[5,7-dimethyl-2-butyl-6(1H)-cycloheptimidazolon-1-yl]methyl]-[1,1'-biphenyl]-2-carboxylic acid, ethyl ester;

4'-[[5(7)-phenyl-7(5)-(1-oxo)ethyl-2-butyl-6(1H)-cycloheptimidazolon-1-yl]methyl]-[1,1'-biphenyl]-2-carboxylic acid;

4'-[[7(5)-(1-oxo)ethyl-5(7)-phenyl-2-butyl-6(1H)-cycloheptimidazolon-1-yl]methyl]-[1,1'-biphenyl]-2-carboxylic acid;

4'-[[5,7-dimethyl-2-butyl-6(1H)-cycloheptimidazolon-1-yl]methyl]-[1,1'-biphenyl]-2-carboxylic acid, acetoxymethyl ester;

4'-[[5,7-dimethyl-2-butyl-6(1H)-cycloheptimidazolon-1-yl]methyl]-[1,1'-biphenyl]-2-carboxylic acid, 1-acetoxy-1-methyl ester;

4'-[[5,7-difluoro-2-propyl-6(1H)-cycloheptimidazolon-1-yl]methyl]-[1,1'-biphenyl]-2-carboxylic acid;

4'-[[5,7-dichloro-2-propyl-6(1H)-cycloheptimidazolon-1-yl]methyl]-[1,1'-biphenyl]-2-carboxylic acid;

4'-[[5,7-dibromo-2-propyl-6(1H)-cycloheptimidazolon-1-yl]methyl]-[1,1'-biphenyl]-2-carboxylic acid;

4'-[[5,7-diiodo-2-propyl-6(1H)-cycloheptimidazolon-1-yl]methyl]-[1,1'-biphenyl]-2-carboxylic acid;

4'-[[5,7-dihydroxy-2-propyl-6(1H)-cycloheptimidazolon-1-yl]methyl]-[1,1'-biphenyl]-2-carboxylic acid;

4'-[[5,7-dimethoxy-2-propyl-6(1H)-cycloheptimidazolon-1-yl]methyl]-[1,1'-biphenyl]-2-carboxylic acid;

4'-[[5,7-dipropoxy-2-propyl-6(1H)-cycloheptimidazolon-1-yl]methyl]-[1,1'-biphenyl]-2-carboxylic acid;

4'-[[5,7-diphenoxy-2-propyl-6(1H)-cycloheptimidazolon-1-yl]methyl]-[1,1'-biphenyl]-2-carboxylic acid;

4'-[[5,7-dithiomethyl-2-propyl-6(1H)-cycloheptimidazolon-1-yl]methyl]-[1,1'-biphenyl]-2-carboxylic acid;

4'-[[5,7-dithiophenyl-2-propyl-6(1H)-cycloheptimidazolon-1-yl]methyl]-[1,1'-biphenyl]-2-carboxylic acid;

4'-[[5,7-dicyano-2-propyl-6(1H)-cycloheptimidazolon-1-yl]methyl]-[1,1'-biphenyl]-2-carboxylic acid;

4'-[[5,7-dinitro-2-propyl-6(1H)-cycloheptimidazolon-1-yl]methyl]-[1,1'-biphenyl]-2-carboxylic acid;

4'-[[5,7-diphenyl-2-propyl-6(1H)-cycloheptimidazolon-1-yl]methyl]-[1,1'-biphenyl]-2-carboxylic acid;

4'-[[5,7-diformyl-2-propyl-6(1H)-cycloheptimidazolon-1-yl]methyl]-[1,1'-biphenyl]-2-carboxylic acid;

4'-[[5-hydroxy-7-chloro-2-propyl-6(1H)-cycloheptimidazolon-1-yl]methyl]-[1,1'-biphenyl]-2-carboxylic acid;

4'-[[5-chloro-7-hydroxy-2-propyl-6(1H)-cycloheptimidazolon-1-yl]methyl]-[1,1'-biphenyl]-2-carboxylic acid;

4'-[[5-carboxylic acid-7-methoxymethyl-2-propyl-6(1H)-cycloheptimidazolon-1-yl]methyl]-[1,1'-biphenyl]-2-carboxylic acid;

4'-[[5-methoxymethyl-7-carboxylic acid-2-propyl-6(1H)-cycloheptimidazolon-1-yl]methyl]-[1,1'-biphenyl]-2-carboxylic acid;

4'-[[5,7-dicarboxylic acid-2-propyl-6(1H)-cycloheptimidazolon-1-yl]methyl]-[1,1'-biphenyl]-2-carboxylic acid;

4'-[[5,7-dimethoxycarbonyl-2-propyl-6(1H)-cycloheptimidazolon-1-yl]methyl]-[1,1'-biphenyl]-2-carboxylic acid;

4'-[[5,7-diethoxycarbonyl-2-propyl-6(1H)-cycloheptimidazolon-1-yl]methyl]-[1,1'-biphenyl]-2-carboxylic acid;

4'-[[5,7-dibenzyloxycabonyl-2-propyl-6(1H)-cycloheptimidazolon-1-yl]methyl]-[1,1'-biphenyl]-2-carboxylic acid;

4'-[[5,7-dicarboxamide-2-propyl-6(1H)-cycloheptimidazolon-1-yl]methyl]-[1,1'-biphenyl]-2-carboxylic acid;

4'-[[5,7-di-N-methylcarboxamide-2-propyl-6(1H)-cycloheptimidazolon-1-yl]methyl]-[1,1'-biphenyl]-2-carboxylic acid;

4'-[[5,7-di-N-ethylcarboxamide-2-propyl-6(1H)-cycloheptimidazolon-1-yl]methyl]-[1,1'-biphenyl]-2-carboxylic acid;

4'-[[5,7-dibenzoyl-2-propyl-6(1H)-cycloheptimidazolon-1-yl]methyl]-[1,1'-biphenyl]-2-carboxylic acid;

4'-[[5(7)-isopropyl-7(5)phenyl-2-propyl-6(1H)-cycloheptimidazolon-1-yl]-methyl]-[1,1'-biphenyl]-2-carboxylic acid;

4'-[[5(7)-hydroxy-7(5)chloro-2-propyl-6(1H)-cycloheptimidazolon-1-yl]-methyl]-[1,1'-biphenyl]-2-carboxylic acid;

4'-[[5(7)-carboxy-7(5)methoxymethyl-2-propyl-6(1H)-cycloheptimidazolon-1-yl]methyl]-[1,1'-biphenyl]-2-carboxylic acid;

4'-[[5(7)-hydrido-7(5)benzyl-2-propyl-6(1H)-cycloheptimidazolon-1-yl]-methyl]-[1,1'-biphenyl]-2-carboxylic acid;

4'-[[5(7)-isopropyl-7(5)phenyl-2-propyl-6(1H)-cycloheptimidazolon-1-yl]-methyl]-[1,1'-biphenyl]-2-carboxylic acid;

4'-[[5,7-dimethyl-2-propyl-6(1H)-cycloheptimidazolon-1-yl]methyl]-[1,1'-biphenyl]-2-carboxylic acid, methyl ester;

4'-[[5,7-diethoxycarbonyl-2-propyl-6(1H)-cycloheptimi-dazolon-1-yl]methyl]-[1,1'-biphenyl]-2-carboxylic acid, ethyl ester;

4'-[[5,7-dimethyl-2-propyl-6(1H)-cycloheptimidazolon-1-yl]methyl]-[1,1'-biphenyl]-2-carboxylic acid, ethyl ester;

4'-[[5(7)-phenyl-7(5)-(1-oxo)ethyl-2-propyl-6(1H)-cycloheptimidazolon-1-yl]methyl]-[1,1'-biphenyl]-2-carboxylic acid;

4'-[[7(5)-(1-oxo)ethyl-5(7)-phenyl-2-propyl-6(1H)-cycloheptimidazolon-1-yl]methyl]-[1,1'-biphenyl]-2-carboxylic acid;

4'-[[5,7-dimethyl-2-propyl-6(1H)-cycloheptimidazolon-1-yl]methyl]-[1,1'-biphenyl]-2-carboxylic acid, acetoxymethyl ester;

4'-[[5,7-dimethyl-2-propyl-6(1H)-cycloheptimidazolon-1-yl]methyl]-[1,1'-biphenyl]-2-carboxylic acid, 1-acetoxy-1-methyl ester;

1-{2'-[(tetrazol-5-yl)-biphenyl-4-yl]methyl}-2-propyl-cycloheptimidazolone;

1-{2'-[(tetrazol-5-yl)-biphenyl-4-yl]methyl}-2-butylcycloheptimidazolone;

1-{2'-[(tetrazol-5-yl)-biphenyl-4-yl]methyl}-2-pentylcycloheptimidazolone;

1-{2'-[(tetrazol-5-yl)-biphenyl-4-yl]methyl}-2-hexylcycloheptimidazolone;

1-{2'-[(tetrazol-5-yl)-biphenyl-4-yl]methyl}-2-propyl-5,7-dimethyl-cycloheptimidazolone;

1-{2'-[(tetrazol-5-yl)-biphenyl-4-yl]methyl}-2-butyl-5,7-dimethyl-cycloheptimidazolone;

1-{2'-[(tetrazol-5-yl)-biphenyl-4-yl]methyl}-2-pentyl-5,7-dimethyl-cycloheptimidazolone;

1-{2'-[(tetrazol-5-yl)-biphenyl-4-yl]methyl}-2-hexyl-5,7-dimethyl-cycloheptimidazolone;

1-{2'-[(tetrazol-5-yl)-biphenyl-4-yl]methyl}-2-propyl-5,7-diphenyl-cycloheptimidazolone;

1-{2'-[(tetrazol-5-yl)-biphenyl-4-yl]methyl}-2-butyl-5,7-diphenyl-cycloheptimidazolone;

1-{2'-[(tetrazol-5-yl)-biphenyl-4-yl]methyl}-2-pentyl-5,7-diphenyl-cycloheptimidazolone;

1-{2'-[(tetrazol-5-yl)-biphenyl-4-yl]methyl}-2-hexyl-5,7-diphenyl-cycloheptimidazolone;

1-{2'-[(tetrazol-5-yl)-biphenyl-4-yl]methyl}-2-propyl-5,7-dichloro-cycloheptimidazolone;

1-{2'-[(tetrazol-5-yl)-biphenyl-4-yl]methyl}-2-butyl-5,7-dichloro-cycloheptimidazolone;

1-{2'-[(tetrazol-5-yl)-biphenyl-4-yl]methyl}-2-pentyl-5,7-dichloro-cycloheptimidazolone;

1-{2'-[(tetrazol-5-yl)-biphenyl-4-yl]methyl}-2-hexyl-5,7-dichloro-cycloheptimidazolone;

1-{2'-[(tetrazol-5-yl)-biphenyl-4-yl]methyl}-2-propyl-5,7-cycloheptimidazolone-dicarboxylic acid, dimethylester;

1-{2'-[(tetrazol-5-yl)-biphenyl-4-yl]methyl}-2-butyl-5,7-cycloheptimidazolone-dicarboxylic acid, dimethylester;

1-{2'-[(tetrazol-5-yl)-biphenyl-4-yl]methyl}-2-pentyl-5,7-cycloheptimidazolone-dicarboxylic acid, dimethylester;

1-{2'-[(tetrazol-5-yl)-biphenyl-4-yl]methyl}-2-hexyl-5,7-cycloheptimidazolone-dicarboxylic acid, dimethylester;

1-{2'-[(tetrazol-5-yl)-biphenyl-4-yl]methyl}-2-propyl-5,7-cycloheptimidazolone-dicarboxylic acid, diethylester;

1-{2'-[(tetrazol-5-yl)-biphenyl-4-yl]methyl}-2-butyl-5,7-cycloheptimidazolone-dicarboxylic acid, diethylester;

1-{2'-[(tetrazol-5-yl)-biphenyl-4-yl]methyl}-2-pentyl-5,7-cycloheptimidazolone-dicarboxylic acid, diethylester;

1-{2'-[(tetrazol-5-yl)-biphenyl-4-yl]methyl}-2-hexyl-5,7-cycloheptimidazolone-dicarboxylic acid, diethylester; and 1-{2'-[(tetrazol-5-yl)-biphenyl-4-yl]methyl}-2-butyl-5,7-dichloro-cycloheptimidazolone.

GENERAL SYNTHETIC PROCEDURES

The compounds of the invention can be synthesized according to the following procedures which are modelled upon the family of compounds of formula III. The reactions are performed in a solvent suitable to the reagent, the material employed and the transformation being performed. Some of the steps will involve reagents and substrates with functionality that will require protection.

Method A

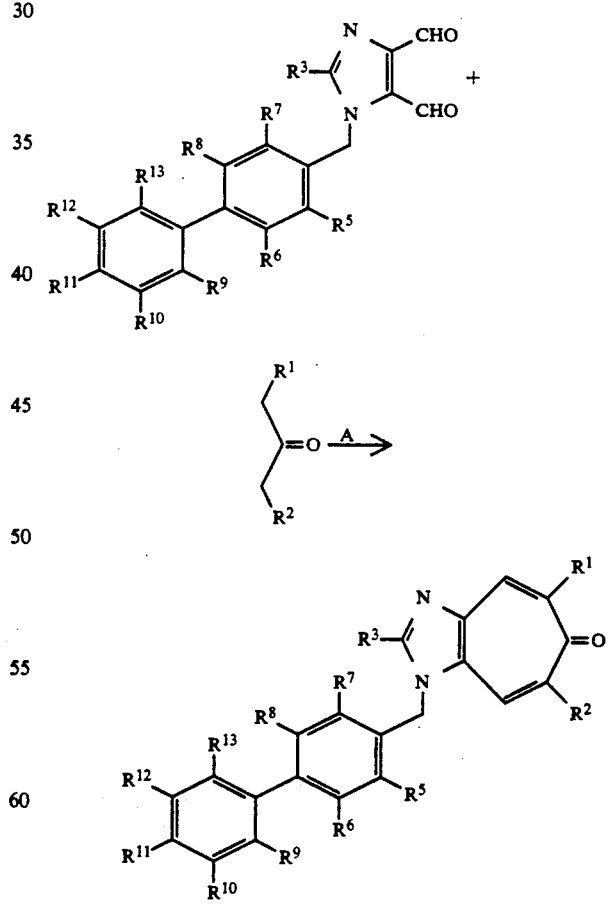

A: Base, aqueous or ethanolic solvent, 0° C. to 80° C., 2-24 hr

The first general method (A) to prepare the compounds of the invention comprises a cyclocondensation reaction between a precursor 4,5-dicarbaldehydeimidazole and a substituted ketone. The condensation reaction is best done in the presence of a base. Among the bases that can be used are trialkylamines, potassium t-butoxide, with the choice being guided by the acidity of the ketone. A variety of solvents can be used to perform this cyclization reaction such as alcohols, dimethylformamide and water. The reaction typically may be carried out in a temperature range from about 0° C. to 80° C. for a period of about 2 to 24 hours.

Method B

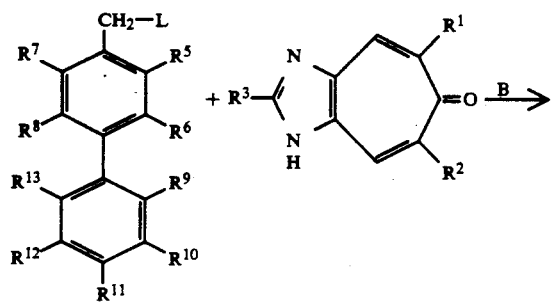

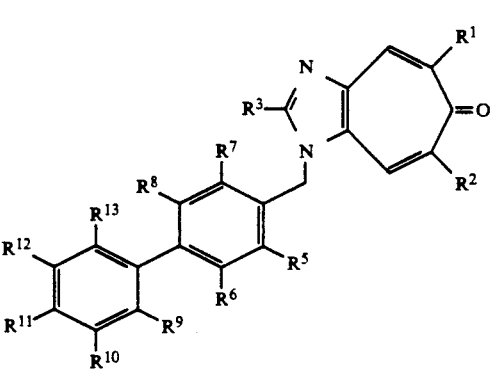

B: Base, non-protic solvent, 0° C. to 120° C., 1 to 24 hr.

A second general method (B) involves N-alkylation of a preformed mono, di, or trisubstituted cycloheptimidazole with an appropriately substituted biphenylalkyl fragment. The biphenylalkyl fragment is substituted on the alkyl group by a leaving group L, for example, a halide, tosylate or mesylate. The reaction may be carried out in the presence of bases, such as trialkylamines, potassium carbonate and potassium t-butoxide. Suitable solvents include high polarity, aprotic solvents such as DMF and DMSO. The reaction is typically carried out at a temperature in a range from about 0° C. to about 120° C. for 1 to 24 hours.

Method C

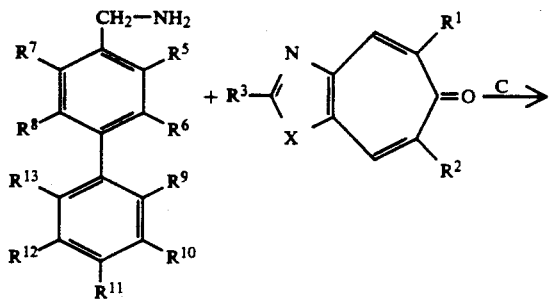

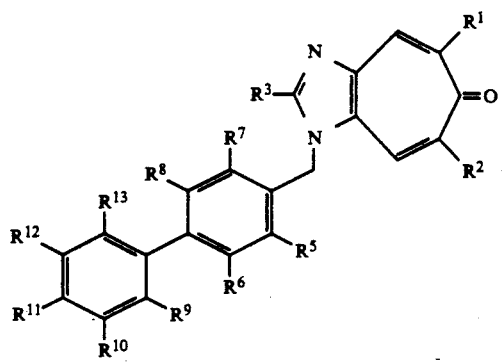

C: heat, non protic solvent.

A third method (C) involves reaction of a tropone derivative having a fused oxazole or thiazole nucleus with an amino alkylbiphenyl derivative. In the event substituents on the fragments are found to be incompatible with the reactions described, then the alternative method described (A, C) may then be used.

Detailed Synthetic Description - Method A

The substituted cycloheptimidazoles can be obtained, as shown in Schemes 1 & 2, starting with appropriately substituted imidazoles-4,5-dicarboxylic acid. These substances are esterified and reduced to the corresponding diols, with or without protection of the imidazole, by means of a complex hydride reducing agent. Once obtained this type of diol is coupled with the desired benzyl halide or benzyl mesylate. The diols obtained are oxidized to a dialdehyde using lead tetracetate, manganese dioxide or an equivalent oxidizing agent. The cycloheptatrienone ring is then built by base-catalyzed condensation with the appropriate ketone. In the case of asymmetrical ketones, a mixture of isomers may be obtained which may be separated by various techniques. Eventually, if necessary, a protecting group on the carboxylic acid function or its bioisosteric equivalent is removed under suitable conditions.

Detailed Synthetic Description
(Method A, scheme A1)

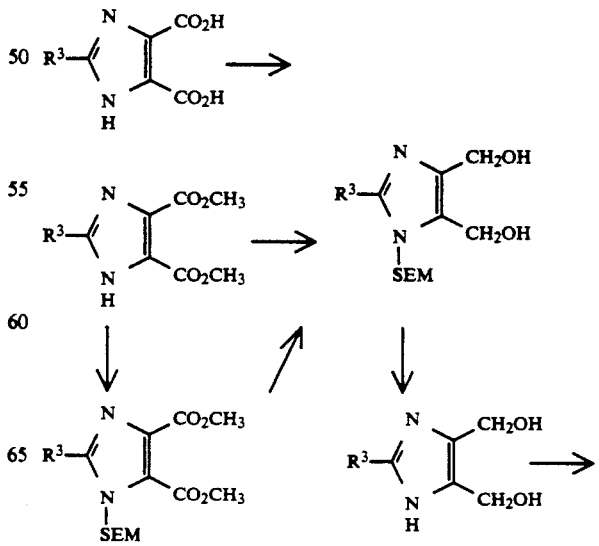

-continued
Detailed Synthetic Description
(Method A, scheme A1)

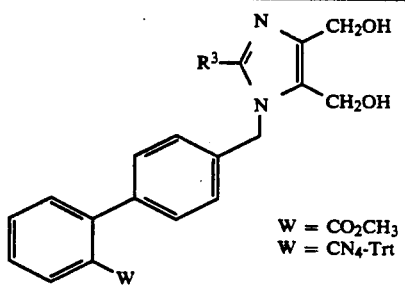

W = CO₂CH₃
W = CN₄-Trt

Detailed Synthetic Description
(Method A, Scheme A2)

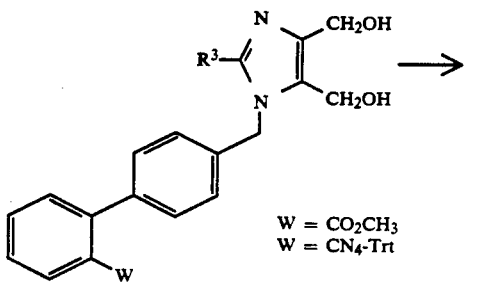

W = CO₂CH₃
W = CN₄-Trt

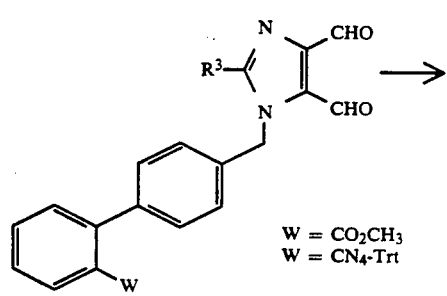

W = CO₂CH₃
W = CN₄-Trt

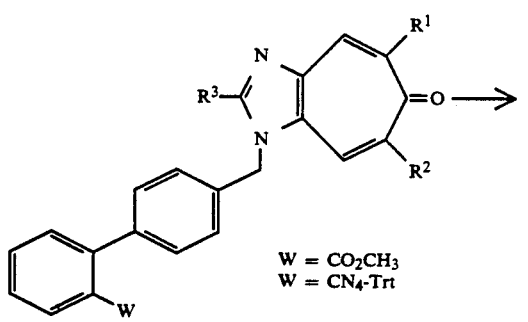

W = CO₂CH₃
W = CN₄-Trt

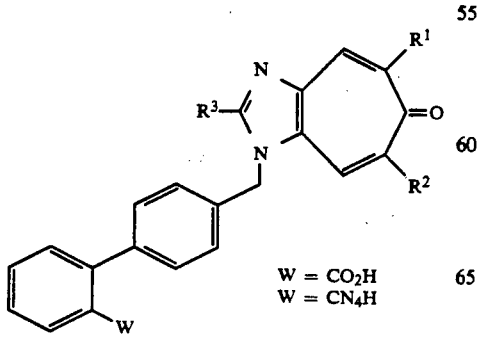

W = CO₂H
W = CN₄H

Detailed Synthetic Description - Method B

The protected diol 3 is obtained as before, but, in this case, the cycloheptatrienone is built before coupling with the benzyl component. Thus, the 2-(trimethylsilyl)ethoxy-methyl-imidazole derivative is oxidized as in Scheme 1 above. The dialdehyde is used to build the cycloheptatrienone ring by base-catalyzed condensation with the appropriate ketone. These derivatives after deprotection can be coupled with the benzylic fragment as in Scheme 3. In the case of asymmetrical ketones, a mixture of isomers may be obtained which may be separated by various techniques. Eventually, if necessary, a protecting group on the carboxylic acid function or its bioisosteric equivalent is removed under suitable conditions.

Detailed Synthetic Description
(Method B, scheme 3)

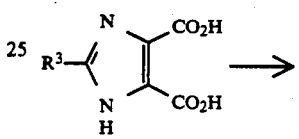

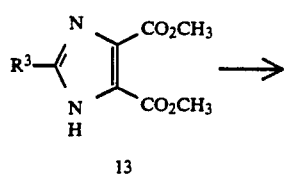
13

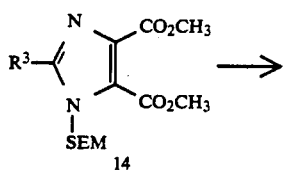
14

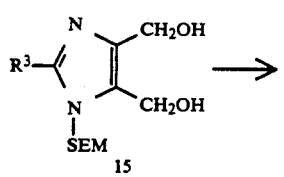
15

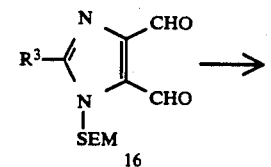
16

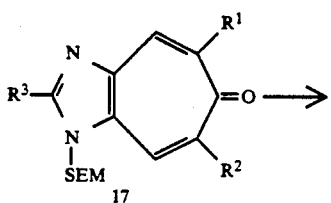
17

-continued
Detailed Synthetic Description
(Method B, scheme 3)

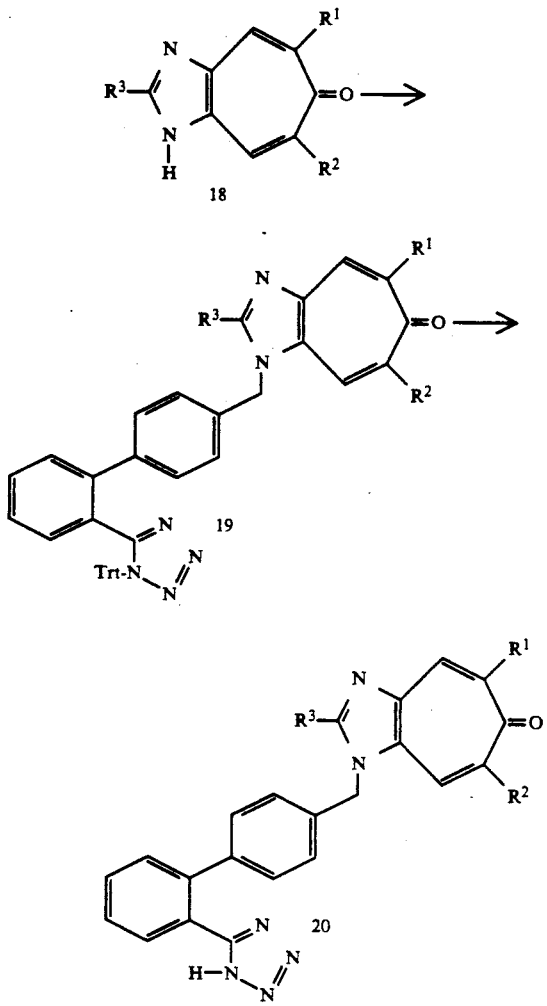

EXAMPLES

The following examples are provided to illustrate the present invention and are not intended to limit the scope thereof. Those skilled in the art will readily understand that known variations of the conditions and processes of the following preparative procedures can be used to prepare these compounds. All temperatures expressed are in degrees centrigrade. Within the foregoing synthetic description and examples which follow, abbreviations have the following meanings:

CHCl₃ = chloroform
DMF = dimethylformamide
DMSO = dimethylsulfoxide
g = gram
MeOH = methanol
min = minute
h = hour
mol = mole
mmol = millimole
MW = molecular weight
TLC = thin layer chromatography
Trt = trityl Other abbreviations may be explained in the text.

EXAMPLE 1

4'-[[5,7-dimethyl-2-butyl-6(1H)-cycloheptimidazolon-1-yl]methyl]-[1,1'-biphenyl]-2-carboxylic acid The target compound was prepared through the intermediates described in Steps (a-i):

Step (a)

2-n-butyl-1H-imidazole-4,5-dicarboxylic acid, dimethyl ester

The starting diacid (32 g, MW 212.2, 0.15 mol) was suspended in 500 ml methanol. Dry hydrogen chloride is bubbled in the reaction for two hours. Toward the end of the first hour, the solid went into solution and the reaction mixture was stirred 60 hr at 25° C. The solvent was removed under vacuum and water was added to the residue. The mixture was made basic by addition of potassium carbonate in an ice bath. The brown oil which formed was extracted with ethyl acetate, dried over potassium carbonate and concentrated. The material obtained weighed 25 g and was homogeneous by TLC (SiO₂, MeOH-CHCl₃/1-5).

¹H NMR (CDCl₃, δ ppm): 9.9 (bs, 1H); 3.8 (s, 6H); 2.65 (m, 2H); 1.6 (m, 2H); 1.25 (m, 2H); 0.8 (m, 3H).

Step (b)

1-[2-(trimethylsilyl)ethoxy]methyl-2-n-butyl-1H-imidazole-4,5-dicarboxylic acid, dimethyl ester The diester 1 from Step (a) (23 g, MW 240, 0.096 mol) was dissolved in 300 ml DMF. Potassium t-butoxide (100 ml of a 1M solution in dry THF) was added through a syringe. The solution was stirred for 15 min at 25° C. [2-(trimethylsilyl)ethoxy]methyl chloride (SEM-chloride, 18.6 ml, 1.1 eq, MW 166, d 0.94) was added and a precipitate instantly formed. The reaction was stirred for 90 min at 25° C. The solvent was removed and the residue partitioned between ethyl acetate and water. The organic extract was dried over K₂CO₃ and concentrated. By TLC (SiO₂, MeOH-CHCl₃/1-10) a single major spot was observed. This crude product (38 g, 106% yield) was used in subsequent steps without further purification.

¹H NMR (CDCl₃, δ ppm): 5.5(s, 2H, N—CH₂—O); 3.95 (s, 6H, CO₂CH₃); 3.5 (t, 2H, C—CH₂—O); 2.9 (t, 2H, C—CH₂—C); 1.75 (m, 2H, C—CH₂—C); 1.4 (m, 2H, C—CH₂—C); 0.95 (t, 3H, CH₃—C); 0.85 (t, 2H, C—CH₂—Si); 0.0 (s, 9H, CH₃—Si).

NB. When necessary, the compound was purified using a Waters Prep 500 and two silicagel cartridges. The mobile phase was 30–70/EtOAc-Hexane. Samples were collected and analyzed by TLC (same solvent system).

Step (c)

1-[2-(trimethylsilyl)ethoxy]methyl-2-n-butyl-4,5-di-(hydroxymethyl)-1H-imidazole The protected diester 2 (10 g, MW 370, 0.027 mol) was dissolved in 50 ml dry diethyl ether. The resulting solution was slowly added through an addition funnel to a solution of lithium aluminium hydride (LAH, 100 ml of a 1M solution in diethyl ether) cooled in an ice-/water bath. After 2 h stirring at 0°-5° C., a precipitate was observed and the reaction mixture was stirred at 25° C. for one more hour. The excess of LAH was decomposed by adding 3.77 ml of water, 3.77 ml 15% sodium hydroxide, and 11.3 ml water. The resulting mixture was filtered and the remaining gummy salts were washed with 300 ml tetrahydrofuran. The filtrate and tetrahydrofuran washing were combined and concentrated. The remaining oil weighed 7 g. A white solid (mp 81–82) was obtained from the diethylether.

$^1$H NMR (CDCl$_3$, δ ppm): 5.3(s, 2H, N—CH$_2$—O); 4.65 (s, 2H, C—CH$_2$—O); 4.55 (s, 2H, C—CH$_2$—O); 3.55 (t, 2H, C—CH$_2$—O); 2.7 (t, 2H, C—CH$_2$—C); 1.75 (m, 2H, C—CH$_2$—C); 1.45 (m, 2H, C—CH$_2$—C); 0.95 (t, 3H, CH$_3$—C); 0.9 (t, 2H, C—CH$_2$—Si); 0.0 (s, 9H, CH$_3$—Si).

Step (d)

2-n-butyl-4,5-di-(hydroxymethyl)-1H-imidazole

The protected diol (7 g) was dissolved in 50 ml 3N HCl and 50 ml ethanol. The solution was refluxed for 3 hours and the azeotrope then removed by distillation under vacuum. Water (50 ml) was added and the pH was brought to basicity (pH 9) with potassium carbonate. The precipitate was collected and dried under vacuum to yield 3.4 g (85% yield) of the deprotected diol.

$^1$H NMR (DMSO-d6, δ ppm): 11.5 (bs, 1H); 4.2 (bs, 4H); 2.45 (t, 2H); 1.6 (m, 2H); 1.3 (m, 2H); 1.85 (t, 3H).

Step (e)

2-n-butyl-4,5-di-(hydroxymethyl)-1H-imidazole

To a solution of the diester (80 g, 0.33 mol) in anhydrous THF (300 ml) at 0° C. were added 940 ml of a 1M LiAlH$_4$ solution in diethyl ether. The reaction mixture was stirred at 25° C. for 3 hours under nitrogen. The excess of hydride was destroyed with water and sodium hydroxyde. The aluminate salts were filtered off and rinsed with THF. The THF was evaporated under reduced pressure to a yellow-orange solid (12.75 g). The solid was identified as the desired diol by proton NMR.

Step (f)

4'-[[2-butyl-4,5-bis(hydroxymethyl)-1H-imidazol-1yl]methyl]-[1,1'-biphenyl]-2-carboxylic acid, methyl ester Potassium t-butoxide (62 ml of 1M solution in THF) was added to a solution of the diol 4 (11.4 g, mw=184, 0.062 mol) in 300 ml DMF under a nitrogen blanket and the resulting solution stirred at 25° C. for 15 minutes. The 4'-(bromomethyl)-[1,1'-biphenyl]-2-carboxylic acid, methyl ester (20.8 g, 1.1 eq, MW 305, 68 mmol) was added and the reaction was stirred for two hours at 25° C. The solvents were removed and the residue partitioned between water and ethyl acetate. The residue from the ethyl acetate extract (20 g) was chromatographed on silica gel with 5% methanol in ethyl acetate. The desired diol (9 g) was obtained as a solid.

$^1$H NMR (CDCl$_3$, δ ppm): 7.85 (d, 1H); 7.5 (t, 1H); 7.4 (t, 1H); 7.35 (d, 1H); 7.3 (d, 2H); 7.0 (d, 2H); 5.25 (s, 2H); 4.5+4.6 (s+s, 2H+2H); 3.65 (s, 3H); 3.3 (bs, 2H); 2.60 (t, 2H); 1.65 (m, 2H); 1.35 (m, 2H) 0.85 (t, 3H). MS (calcd C$_{24}$H$_{28}$N$_2$O$_4$, found M+H+): 408.5, 409.

Step (g)

4'-[[2-butyl-4,5-bis(carboxaldehyde)-1H-imidazol-1-yl]methyl]-[1,1'-biphenyl]-2-carboxylic acid, methyl ester The dihydroxymethyl-imidazole (MW 408; 1.5 g; 3.67 mmol) was dissolved in 40 ml anhydrous pyridine. Lead tetraacetate (MW 443; 3.91 g; 8.8 mmol; 2.5 eq) was added and the mixture was stirred at 25° C. for 4 hours. Volatiles were removed in vacuum and the residue was partitioned between aqueous potassium carbonate and ethyl acetate. The organic phase was dried and concentrated. This yielded 0.7 g of the desired dialdehyde as an oil.

$^1$H NMR (CDCl$_3$, δ ppm): 10.35 (s, 1H); 10.1 (s, 1H); 7.85 (d, 1H); 7.6 (t, 1H); 7.5 (t, 1H); 7.4 (d, 1H); 7.3 (d, 2H); 7.1 (d, 2H); 5.7 (s, 2H); 3.60 (s, 3H); 2.7 (t, 2H, C—CH$_2$—C); 1.65 (m, 2H, C—CH$_2$—C); 1.30 (m, 2H); 0.95 (t, 3H).

Step (h)

4'-[[5,7-dimethyl-2-butyl-6(1H)-cycloheptimidazolon-1-yl]methyl]-[1,1'-biphenyl]-2-carboxylic acid, ethyl ester In 5 ml of dry ethanol, 2.05 ml of a 2M solution of n-butyl lithium (5.1 mmol, 4 eq) was slowly added through a syringe. A mixture of 108 mg (1.26 mmol, MW 86.1, 1 eq.) of 3-pentanone and 500 mg (1.25 mmol, MW 396, 1 eq) of the dialdehyde from step (g) was added over a 30 min period. After stirring at 25° C. for 16 h, the solvent was removed under vacuum. The residue was partitioned between ethyl acetate and 2N aqueous HCl. The organic phase was then washed with aqueous potassium carbonate, dried on sodium sulfate and concentrated in vacuo. The residue (0.5 g) was chromatographed on silica gel with 2-1/EtOAc-Hexane. The main component (Rf=0.6, SiO$_2$, EtOAc) was isolated as a solid (150 mg) by trituration in diethyl ether and identified as the desired product by proton NMR and mass spectroscopy.

$^1$H NMR (CDCl$_3$, δ ppm): 8.0(s, 1H); 7.85 (d, 1H); 7.55 (t, 1H); 7.45 (d+s; 1H+1H); 7.25(d+s, 2H+1H); 7.0 (d, 2H); 5.4 (s, 2H); 4.05 (q, 2H); 2.85 (t, 2H); 2.35+2.4 (s+s, 3H+3H); 1.85 (m, 2H); 1.45 (m, 2H); 1.0+0.95 (t+t, 3H+3H).

MS (calcd C$_{30}$H$_{32}$N$_2$O$_3$, found M+H+): 468, 469.

Step (i)

4'-[[5,7-dimethyl-2-butyl-6(1H)-cycloheptimidazolon-1-yl]methyl]-[1,1'-biphenyl]-2-carboxylic acid An aliquot of the ethyl ester (100 mg) was hydrolyzed by stirring it in a mixture of 2 ml of 10% sodium hydroxide and 2 ml of ethanol for 6 h at 25° C. for 1 h at 100° C. The azeotrope was distilled off, water (10 ml) was added and the resulting solution slowly acidified to pH 2.5 with HCl 2N. The resulting precipitated acid was isolated (60 mg).

$^1$H NMR (DMSO-d6, δ ppm): 8.0(s, 1H); 7.95 (s, 1H); 7.75 (d, 1H); 7.55 (t, 1H); 7.45(t,1H); 7.35 (d, 2H); 7.05 (d,2H); 5.6 (s,2H); 2.80 (t, 2H); 2.25+2.4 (s, 6H); 1.65 (m, 2H); 1.35 (m, 2H); 0.85 (t, 3H). MS (calcd C$_{28}$H$_{28}$N$_2$O$_3$, found M+H+): 440.5, 441.

EXAMPLE 2

[1-[2-(trimethylsilyl)ethoxy]methyl]-2-butyl-6(1H)-cycloheptimidazolone

The target compound was prepared through the intermediates described in Steps (a-i), of which, Steps (a-g) are common with Example 1.

Step (h)

4'-[[5,7-diethoxycarbonyl-2-butyl-6(1H)-cycloheptimidazolon-1-yl]methyl]-[1,1'-biphenyl]-2-carboxylic acid, methyl ester To a stirred solution of 400 mg of the dialdehyde 6 of Example 1 Step (g), (1 mmol, MW 394), were added 220 mg of dimethyl-3-oxoglutarate (1.1 mmol, MW 202) and 3 drops of triethylamine. The reaction mixture was stirred 20 hours at 40° C. After solvent removal and aqueous work-up (EtOAc), the residual oil (650 mg) was chromatographed on silica gel with EtOAc:Hex/1:1 and 300 mg of pure compound was isolated.

$^1$H NMR (CDCl$_3$, δ ppm): 8.3(s, 1H); 7.95(s, 1H); 7.85 (d, 1H); 7.55 (t, 1H); 7.45 (d; 1H); 7.35(d,1H); 7.30(d, 2H); 7.0 (d, 2H); 5.4 (s,2H); 4.35 (m,4H); 3.62 (s, 3H); 2.85 (t,2H); 1.85 (m, 2H); 1.45 (m, 2H); 1.35 (m, 6H); 0.95 (t, 3H).

MS (calcd C₃₃H₃₉N₂O₇, found M+H+): 570, 571.

Step (i)

4'-[[5,7-dicarboxy-2-butyl-6(1H)-cycloheptimidazolon-1-yl]methyl]-[1,1'-biphenyl]-2-carboxylic acid An aliquot of the triester from Step (h) (300 mg) was hydrolyzed by stirring it in a mixture of 12 ml of 10% sodium hydroxide and 12 ml of ethanol for 6 h at 40° C. The azeotrope was distilled off, water (30 ml) was added and the resulting solution slowly acidified to pH 3 with HCl 2N. The resulting precipitated acid was isolated (mp 186, decomp.).

¹H NMR (CDCl₃+DMSO-d6, δ ppm): 8.3(s, 1H); 7.95(s, 1H); 7.85 (d, 1H); 7.55 (t, 1H); 7.45 (d; 1H); 7.35(d,1H); 7.30(d, 2H); 7.0 (d, 2H); 5.4 (s,2H); 4.35 (m,4H); 3.62 (s, 3H); 2.85 (t,2H); 1.85 (m, 2H); 1.45 (m, 2H); 1.35 (m, 6H); 0.95 (t, 3H).

MS (calcd C₃₃H₃₉N₂O₇, found M+H+): 500.1, 501

EXAMPLE 3

4'-[[2-butyl-6(1H)-cycloheptimidazolon-1-yl]methyl]-[1,1'-biphenyl]-2-carboxylic acid The target compound was prepared through the intermediates described in Steps (k-o) and Steps (a, b and c) common with Example 1.

Step (k)

1-[2-(trimethylsilyl)ethoxy]methyl-2-n-butyl-4,5-di(-carboxaldehyde)-1H-imidazole The dihydroxymethyl-imidazole (MW 270; 16 g; 0.059 mol) was dissolved in 200 ml pyridine. Lead tetraacetate (MW 443; 64 g; 2.5 eq) was added and the mixture was stirred at 25° C. for 3 hours. Volatiles were removed in vacuum and the residue was partitioned between aqueous potassium carbonate and ethyl acetate. The organic phase was dried, concentrated and chromatographed on silica gel (12 g of crude on 300 g of silica gel; ethyl acetate:hexane/30:70). This yielded 7 g of the desired dialdehyde as an oil.

¹H NMR (CDCl₃, δ ppm): 10.35(s, 1H); 10.05 (s, 1H); 5.78 (s, 2H, N—CH₂—O); 3.60 (t, 2H, C—CH₂—O); 2.8 (t, 2H, C—CH₂—C); 1.85 (m, 2H, C—CH₂—C); 1.45 (m, 2H, C—CH₂—C); 0.95 (t, 3H, CH₃—C); 0.9 (t, 2H, C—CH₂—Si); 0.0 (s, 9H, CH₃—Si).

Step (l)

[1-[2-(trimethylsilyl)ethoxy]methyl]-2-butyl-6(1H)-cycloheptimidazolone

The dialdehyde (0.9 g, 3.2 mmol) and 260 ul of acetone (1.1 eq, MW 58.08, d=0.79) were mixed in ten milliliters of anhydrous ethyl alcohol. This solution was slowly dripped into 13 ml of potassium t-butoxide (1.0M solution). The reaction mixture was stirred at 25° C. for three hours and refluxed for thirty minutes. The volatiles were removed under vacuum and the residue was partitionned between ether and water (pH=9). The ether solution was concentrated to give a brown oil (~1 g).

¹H NMR (CDCl₃, δ ppm): 7.7 (d, 1H); 7.5 (d, 1H); 7 (m, 2H); 5.48 (s, 2H, N—CH₂—O); 3.60 (t, 2H, C—CH₂—O); 2.9 (t, 2H, C—CH₂—C); 1.85 (m, 2H, C—CH₂—C); 1.45 (m, 2H, C—CH₂—C); 0.95 (t, 3H, CH₃—C); 0.9 (t, 2H, C—CH₂—Si); 0.0 (s, 9H, CH₃—Si).

Step (m)

2-butyl-6(1H)-cycloheptimidazolone

The crude SEM-protected cycloheptimidazolone was dissolved in 5 ml ethanol and 5 ml 3N hydrochloric acid and the solution was refluxed for four and an half hours. Volatiles were removed under vacuum. The residue was added to 10 ml 0.1N hydrochloric acid and the pH was brought to 9 with potassium carbonate. An oil formed which was extracted with acetone. The extract was dried over potassium carbonate and concentrated. The residue was dissolved in methanol and the precipitate that formed was collected by filtration.

¹H NMR (DMSO-d6, δ ppm): 7.55 (d, 2H); 6.5 (d, 2H); 2.7 (t, 2H); 1.7 (m, 2H); 1.55(m, 2H); 1.9 (t, 3H).

Step (n)

4'-[[2-butyl-6(1H)-cycloheptimidazolon-1-yl]methyl]-[1,1'-biphenyl]-2-carboxylic acid, methyl ester The cycloheptatrienone (500 mg, mw 202, 2.5 mmol) was dissolved in 15 ml of dimethtylformamide. A solution of potassium t-butoxide in tetrahydrofuran (2.5 ml of a 1.0M solution) was added and the resulting mixture was stirred for two hours at 25° C. The solvents were removed under vacuum and the residue was partitioned between water and ethyl acetate. The organic phase was dried over potassium carbonate and concentrated. The residue upon trituration with ether/hexane gave a brown solid which was removed by filtration. The filtrate was purified by chromatography on a silica gel column using chloroform as eluant. The desired ester was collected as an oil (200 mg).

H NMR (CDCl₃+DMSO-d6, δ ppm): 7.85(m, 2H); 7.75(d, 1H); 7.55 (t, 1H); 7.5–7.3 (m, 5H); 7.05 (d; 2H); 6.9 (m,1H); 5.4 (s, 2H); 3.62 (s, 3H); 2.85 (t, 2H); 1.85 (m, 2H); 1.45 (m, 2H); 0.95 (t, 3H).

Step (o)

4'-[[2-butyl-6(1H)-cycloheptimidazolon-1-yl]methyl]-[1,1'-biphenyl]-2-carboxylic acid An aliquot of the methyl ester from Step (n) (200 mg) was hydrolyzed by stirring it in a mixture of 5 ml of 10° sodium hydroxide and 5 ml ethanol for 4 hr at 25° C. and 1 hr at 100° C. The azeotrope was distilled off, water (10 ml) was added and the resulting solution slowly acidified to pH 2.5 with 2N HCl. The resulting precipitated acid was isolated (60 mg).

¹H NMR (DMSO-d6, δ ppm): 7.75 (m, 3H); 7.55 (t, 1H); 7.45 (t,1H); 7.35 (m, 5H); 7.05 (d, 2H); 6.85 (t, 2H); 5.6 (s,2H); 2.85 (t, 2H); 1.65 (m, 2H); 1.35 (m, 2H); 0.85 (t, 3H).

MS (calcd Cl₂₆H₂₄N₂O₃, found M+H+): 412.5, 413.

EXAMPLES 4–19

Example compounds 4–19 listed below, were synthesized in accordance with the foregoing methods A–C. The specific method used to prepare these examples is identified in Table I.

EXAMPLE 4

4'-[[5,7-dicarboxy-2-propyl-6(1H)-cycloheptimidazolon-1-yl]methyl]-1,1'-biphenyl]-2-carboxylic acid;

EXAMPLE 5

4'-[[2-propyl-6(1H)-cycloheptimidazolon-1-yl]methyl]-[1,1'-biphenyl]-2-carboxylic acid;

EXAMPLE 6

4'-[[5,7-dimethyl-2-pentyl-6(1H)-cycloheptimidazolon-1-yl]methyl]-[1,1'-biphenyl]-2-carboxylic acid;

EXAMPLE 7

4'-[[5,7-diphenyl-2-butyl-6(1H)-cycloheptimidazolon-1-yl]methyl]-[1,1'-biphenyl]-2-carboxylic acid;

EXAMPLE 8

4'-[[5,7-dichloro-2-butyl-6(1H)-cycloheptimidazolon-1-yl]methyl]-[1,1'-biphenyl]-2-carboxylic acid;

EXAMPLE 9

4'-[[5,7-di-n-propyl-2-butyl-6(1H)-cycloheptimidazolon-1-yl]methyl]-[1,1'-biphenyl]-2-carboxylic acid;

EXAMPLE 10

4'-[[5(7)-isopropyl-7(5)phenyl-2-butyl-6(1H)-cycloheptimidazolon-1-yl]methyl]-[1,1'-biphenyl]-2-carboxylic acid;

EXAMPLE 11

4'-[[5(7)-hydroxy-7(5)chloro-2-butyl-6(1H)-cycloheptimidazolon-1-yl]methyl]-[1,1'-biphenyl]-2-carboxylic acid;

EXAMPLE 12

4'-[[5(7)-carboxy-7(5)methoxymethyl-2-butyl-6(1H)-cycloheptimidazolon-1-yl]methyl]-[1,1'-biphenyl]-2-carboxylic acid;

EXAMPLE 13

4'-[[5(7)-hydrido-7(5)benzyl-2-propyl-6(1H)-cycloheptimidazolon-1-yl]methyl]-[1,1'-biphenyl]-2-carboxylic acid;

EXAMPLE 14

4'-[[5(7)-benzyl-7(5)hydrido-2-butyl-6(1H)-cycloheptimidazolon-1-yl]methyl]-[1,1'-biphenyl]-2-carboxylic acid;

EXAMPLE 15

4'-[[5,7-dimethyl-2-butyl-6(1H)-cycloheptimidazolon-1-yl]methyl]-[1,1'-biphenyl]-2-carboxylic acid, methyl ester;

EXAMPLE 16

4'-[[5,7-diethoxycarbonyl-2-butyl-6(1H)-cycloheptimidazolon-1-yl]methyl]-[1,1'-biphenyl]-2-carboxylic acid, ethyl ester

EXAMPLE 17

4'-[[5,7-dimethyl-2-butyl-6(1H)-cycloheptimidazolon-1-yl]methyl]-[1,1'-biphenyl]-2-carboxylic acid, ethyl ester;

EXAMPLE 18

4'-[[5(7)-phenyl-7(5)-acetyl-2-butyl-6(1H)-cycloheptimidazolon-1-yl]methyl]-[1,1'-biphenyl]-2-carboxylic acid;

EXAMPLE 19

4'-[[5(7)-acetyl-7(5)-phenyl--2-butyl-6(1H)-cycloheptimidazolon-1-yl]methyl]-[1,1'-biphenyl]-2-carboxylic acid;

EXAMPLE 20

1-{2'-[(tetrazol-5-yl)-biphenyl-4-yl]methyl}-2-pentyl-5,7-dimethyl-cycloheptimidazolone The target compound was prepared through the intermediates described in Steps (a, b, c, and k-o) listed below.

2-n-pentyl-1H-imidazole-4,5-dicarboxylic acid, dimethyl ester
Step (a)
The procedure of Example 1 was followed substituting 2-n-pentyl-1H-imidazole-4,5-dicarboxylic acid (30 g). The material obtained weighed 25 g and was homogeneous by TLC (SiO$_2$, MeOH-CHCl$_3$/1-5).

$^1$H NMR (CDCl$_3$, δ ppm): 9.9 (bs,1H); 3.8 (s, 6H); 2.85 (m, 2H); 1.6 (m, 2H); 1.25 (m, 4H); 0.85 (m, 3H).

Step (b)
1-[2-(trimethylsilyl)ethoxy]methyl-2-n-butyl-1H-imidazole-4,5-dicarboxylic acid, dimethyl ester-14-

The diester from Step (a) of Example 3 (25 g, MW 254, 0.098 mol) was protected using the procedure described for example 2. This crude product (21 g, 50% yield) after aqueous work-up was used in subsequent steps without further purification.

Step (c)
1-[2-(trimethylsilyl)ethoxy]methyl-2-n-pentyl-4,5-di(-hydroxymethyl)-1H-imidazole The protected diester from Step (b) of Example 3 (21 g) was reduced as described in Example 3. The crude product was purified by silicagel column and obtained as a solid weighing 7 g.

$^1$H NMR (CDCl$_3$, δ ppm): 5.3(s, 2H, N—CH$_2$—O); 4.65 (s, 2H, C—CH$_2$—O); 4.55 (s, 2H, C—CH$_2$—O); 3.55 (t, 2H, C—CH$_2$—O); 2.7 (t, 2H, C—CH$_2$—C); 1.75 (m, 2H, C—CH$_2$—C); 1.35 (m, 4H, C—CH$_2$—C); 0.95 (t, 3H, CH$_3$—C); 0.9 (t, 2H, C—CH$_2$—Si); 0.0 (s, 9H, CH$_3$—Si).

Step (k)
1-[2-(trimethylsilyl)ethoxy]methyl-2-n-butyl-4,5-di(-carboxaldehyde)-1H-imidazole The dihydroxymethyl-imidazole (MW 327; 5.3 g; 16.2 mmol) was dissolved in 200 ml pyridine. Lead tetraacetate (MW 443; 18 g; 40 mmol; 2.5 eq) was added and the mixture was stirred at 25° C. for 3 hours. Volatiles were removed in vacuum and the residue was used without further purification in the next step since NMR showed only the presence of the dialdehyde.

Step (l and m)
2-pentyl-6(1H)-cycloheptimidazolone

An aliquot of 8 mmol of the dialdehyde from Step (k) of Example 3 in 200 ml EtOH was added to an equimolar amount of 3-pentanone (MW 86; 1.7 ml; d=0.814). This mixture was slowly added to 33 ml of 1M potassium t-butoxide in THF. The reaction mixture was stirred at 25° C. for 16 hours and refluxed for four hours. After removal of the solvent under vacuum, the residue was partitioned between water and diethylether. The ether solution was dried over sodium sulfate and concentrated to an oil.

$^1$H NMR (CDCl$_3$, δ ppm): 7.9 (d, 1H); 7.65 (d, 1H); 5.45 (s, 2H, N—CH$_2$—O); 3.60 (t, 2H, C—CH$_2$—O); 2.9 (t, 2H, C—CH$_2$—C); 2.34+2.5 (s+s, 3H+3H, CH$_3$); 1.85 (m, 2H, C—CH$_2$—C); 1.5 (m, 4H, C—CH$_2$—C); 0.95 (t, 3H, CH$_3$—C); 0.9 (t, 2H, C—CH$_2$—Si); 0.0 (s, 9H, CH$_3$—Si).

The crude SEM-protected cycloheptimidazolone was dissolved in 50 ml of ethanol and 50 ml of 3N hydrochloric acid and the solution refluxed for three hours. Volatiles were removed under vacuum. The residue was extracted with chloroform under basic and acidic conditions. TLC showed product in both extracts which were then dried and concentrated. The resulting solid (2.2 g) was chromatographed on silicagel with 5% methanol saturated with ammonia in chloroform. The pure fractions were collected and concentrated to give 1 g of solid. $^1$H NMR (CDCl$_3$, δ ppm): 7.9 (bs, 2H); 2.85 (t, 2H); 2.34+2.5 (s+s, 3H+3H, CH$_3$); 1.85 (m, 2H); 1.40 (m, 4H); 0.9 (t, 3H).

FABMS (calcld for C$_{15}$H$_{20}$N$_2$O, found): 244, 245.2 (M+H).

Step (n)

1-{2'-[N-triphenylmethyl-tetrazol-5-yl)-biphenyl-4-yl]methyl}-2-pentyl-5,7-dimethyl-cycloheptimidazolone An aliquot of 150 mg of the dimethylcycloheptimidazolone (mw 244; 0.61 mmol) was dissolved in 10 ml dry dimethyl formamide. Potassium t-butoxide (0.65 ml; 1M solution) was added and the solution stirred at 25° C. for 20 minutes. An equimolar amount of (N-triphenylmethyl-5-[2(4'-bromomethyl-biphenyl)]-tetrazole (420 mg; MW 476; purity 80%) was added and the resulting solution was stirred at 25° C. for 16 hours. After removal of the solvents under vacuum, the residue was chromatographed on silicagel with 5% ethyl acetate in chloroform and the main product isolated and identified by NMR.

$^1$H NMR (CDCl$_3$, δ ppm): 7.9 (m, 2H); 7,5 (m, 2H); 7.4–6.75 (m, 22H); 5.2 (s, 2H); 2.85 (t, 2H); 2.4 (s, 3H); 2.2 (s, 3H); 1.8 (m, 2H);1.30 (m, 4H); 0.95(t, 3H).

Step (o)

1-{2'-[(tetrazol-5-yl)-biphenyl-4-yl]methyl}-2-pentyl-5,7-dimethyl-cycloheptimidazolone The product obtained above was stirred in 25 ml of a solution of 10% water in acetic acid for 16 hours at 25° C. The solid remaining after removal of the solvents was dissolved in acetone and the desired product precipitated with hexane as a powder. $^1$H NMR (CDCl$_3$, δ ppm): 7.9 (m, 2H); 7,5 (m, 2H); 7.4–6.75 (m, 22H); 5.2 (s, 2H); 2.85 (t, 2H); 2.4 (s, 3H); 2.2 (s, 3H); 1.8 (m, 2H);1.30 (m, 4H); 0.95(t, 3H).

Example compounds, 20–22 as listed below and in Table I, were prepared in accordance with the foregoing procedures.

EXAMPLE 20

1-{2'-[(tetrazol-5-yl)-biphenyl-4-yl]-methyl}-2-pentyl-5,7-dimethyl-cycloheptimidazolone

EXAMPLE 21

1-{2'[(tetrazol-5-yl)-biphenyl-4-yl]-methyl}-2-butyl-cycloheptimidazol-6-one-5,7-dicarboxylic acid, diethyl ester

EXAMPLE 22

1-{2'[(tetrazol-5-yl)-biphenyl-4-yl]-methyl}-2-butyl-5,7-dichloro-cycloheptimidazol-6-one

TABLE I

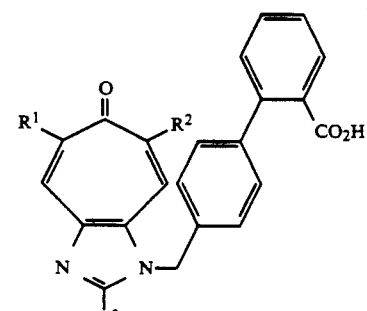

| EX # | R$^1$ | R$^2$ | R$^3$ | Y | Formula | MW M + H$^+$ | Ident. | Synthetic Method |
|---|---|---|---|---|---|---|---|---|
| 1 | CH$_3$ | CH$_3$ | n-But | | C$_{28}$H$_{28}$N$_2$O$_3$ | 440.5 441. | CHN $^1$HNMR | A |
| 2 | CO$_2$H | CO$_2$H | n-But | | C$_{28}$H$_{24}$N$_2$O$_7$ | 500.1 501 | $^1$HNMR | A |
| 3 | H | H | n-But | | C$_{26}$H$_{24}$N$_2$O$_3$ | 412.5 413 | $^1$HNMR | B |
| 4 | CO$_2$H | CO$_2$H | n-Pro | | C$_{27}$H$_{22}$N$_2$O$_7$ | 486.5 487 | CHN $^1$HNMR | A |
| 5 | H | H | n-Pro | | C$_{25}$H$_{22}$N$_2$O$_3$ | 398.5 399.4 | CHN $^1$HNMR | B |
| 6 | CH$_3$ | CH$_3$ | n-Pent | | C$_{29}$H$_{30}$N$_2$O$_3$ | 452.5 453.5 | $^1$HNMR | B |
| 7 | Phe | Phe | n-But | | C$_{38}$H$_{32}$N$_2$O$_3$ | 564.7 565.4 | CHN $^1$HNMR | B |
| 8 | Cl | Cl | n-But | | C$_{26}$H$_{22}$N$_2$O$_3$Cl$_2$ | 481.4 481.1 | CHN $^1$HNMR | B |
| 9 | C$_3$H$_7$ | C$_3$H$_7$ | n-But | | C$_{32}$H$_{36}$N$_2$O$_3$ | 496.6 497 | CHN $^1$HNMR | A |
| *10 | iPro | C$_6$H$_5$ | n-But | | C$_{35}$H$_{34}$N$_2$O$_3$ | 530.7 531 | $^1$HNMR | B |
| *11 | O—H | Cl | n-But | | C$_{26}$H$_{23}$N$_2$O$_4$Cl | 462.9 463.2 | $^1$HNMR | B |
| *12 | CO$_2$H | CH$_2$OCH$_3$ | n-But | | C$_{29}$H$_{28}$N$_2$O$_6$ | 500.5 501.2 | $^1$HNMR | A |
| *13 | H | CH$_2$C$_6$H$_5$ | n-Pro | | C$_{32}$H$_{28}$N$_2$O$_3$ | 488.6 489.5 | $^1$HNMR | B |
| *14 | CH$_2$C$_6$H$_5$ | H | n-Pro | | C$_{32}$H$_{28}$N$_2$O$_3$ | 488. 489.5 | $^1$HNMR | B |

TABLE I-continued

| EX # | R¹ | R² | R³ | Y | Formula | MW M+H⁺ | Ident. | Synthetic Method |
|------|-----|-----|-----|-----|---------|---------|--------|------------------|

[Structure: tropone fused imidazole with biphenyl-CO₂Y substituent]

| 15 | $CH_3$ | $CH_3$ | n-But | $CH_3$ | $C_{29}H_{30}N_2O_3$ | 454.6 455 | CHN ¹HNMR | B |
| 16 | $CO_2C_2H_5$ | $CO_2C_2H_5$ | n-But | $C_2H_5$ | $C_{34}H_{30}N_2O_4$ | 530.6 | ¹HNMR | A |
| 17 | $CH_3$ | $CH_3$ | n-But | $C_2H_5$ | $C_{30}H_{32}N_2O_3$ | 468.6 469 | ¹HNMR | A |
| 18 | $C_6H_5$ | $COCH_3$ | n-But | H | $C_{34}H_{30}N_2O_4$ | 530.6 | CHN ¹HNMR | A |
| 19 | $COCH_3$ | $C_6H_5$ | n-But | H | $C_{34}H_{30}N_2O_4$ | 530.6 | ¹HNMR | A |

[Structure: tropone fused imidazole with biphenyl-tetrazole substituent]

| 20 | $CH_3$ | $CH_3$ | n-Pent | | $C_{29}H_{30}N_6O$ | 478.6 487.5 | ¹HNMR | A |
| 21 | $CO_2C_2H_5$ | $CO_2C_2H_5$ | n-But | | $C_{32}H_{32}N_6O_5$ | 580.5 581 | CHN ¹HNMR | B |
| 22 | Cl | Cl | n-But | | $C_{26}H_{22}N_4O$ | 504.5 505 | CHN ¹HNMR | B |

*regoisomerism not determined

BIOLOGICAL EVALUATION

Angiotensin II Binding Assay

Materials: Angiotensin II (AII) was purchased from Peninsula Labs. ¹²⁵I-angiotensin II (specific activity of 2200 Ci/mmol) was purchased from Du Pont-New England Nuclear. Other chemicals were obtained from Sigma Chemical Co.

AII binding assay: Rat uterine membranes were prepared from fresh tissue. All procedures were carried out at 4° C. Uteri were stripped of fat and homogenized using a Polytron for 25 sec in 20 volumes of ice-cold Dulbecco's phosphate-buffered saline pH 7.5 (Gibso Labs) containing 5 mM EDTA. The homogenate was centrifuged at 1500×g for 20 min., and the supernatant was recentrifuged at 100,000×g for 60 min. The pellet was resuspended in buffer consisting of 2 mM EDTA and 50 mM Tris-HCl, pH 7.5 to a final protein concentration of 4 mg/ml.

Assay tubes contained 0.25 ml of a solution containing 5 mM $MgCl_2$, 2 mM EDTA, 0.5% bovine serum albumin, 50 mM Tris-HCl, pH 7.5 (Buffer A) and ¹²⁵I-AII (approximately 10⁵ cpm) in the absence and in the presence of unlabelled ligand. The reaction was initiated by the addition of 50 μg of membrane protein and the mixture was incubated at 25° C. for 30 min. The incubation was terminated with ice-cold 50 mM Tris-HCl; pH 7.5 and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 μM of unlabelled AII. Specific binding was calculated as total binding minus nonspecific binding. Binding data was analyzed by a nonlinear least-squares curve fitting program.

In vitro mytropic screening assay for AII antagonists

The compounds of the invention were tested for agonist and antagonist activity in rabbit aortic rings. Male New Zealand white rabbits (2–2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C., between a moveable and a fixed stainless steel wire, with the moveable end attached to an FT03 Grass transducer coupled to a Model 7D Grass Polygraph for recording isometric force responses. The bath was filled with 20 ml of oxygenated (95% oxygen/5% carbon dioxide) Krebs solution of the following composition (nM): 130 NaCl, 15 NaHCO$_3$, 15 KCl, 1.2 NaH$_2$PO$_4$, 1.2 MgSO$_4$, 2.5 CaCl$_2$, and 11.4 glucose. The preparations were equilibrated for one hour before approximately one gram of passive tension was placed on the rings. For the agonist assay, the rings were exposed to increasing concentrations of the test compound, at 30 minute intervals, during which time the tissue was washed three times with 20 ml of fresh Krebs solution. For the measurement of antagonistic activity, paired rings from the same rabbits were used; one was exposed to increasing concentrations of AII (at 30 minute intervals), and a second ring was exposed to increasing concentrations of AII in the presence of the test compound which was added five minutes prior to the addition of AII. The concentration response curves for AII in the presence of the antagonist were evaluated in terms of the percent of the maximal contraction of the control ring exposed only to AII. pD2 values for AII were calculated from the AII concentration response curves while pA2s were determined according to Schild.

In vivo pressor screening assay for AII antagonists

Male Sprague Dawley rats weighing 250-300 mgs were anesthetized with Inactin (100 mg/kg), a catheter was inserted into the trachea and the carotid artery and the jugular vein were cannulated. Arterial pressure was measured from the carotid artery cannula and continuously recorded (Gould, Cleveland, OH). The jugular vein cannula was used for injections of angiotensin II (AII), mecamylamine, atropine and the test compound. The animal was allowed to equilibrate for 30 minutes. Mecamylamine (3 mg/kg, 0.3 mg/kg) and atropine (400 µg/kg, 0.3 ml/kg) were then given iv to produce ganglion blockage. These compounds were administered every 90 minutes throughout the screening procedure. Angiotensin II was given in bolus doses (30 µg/kg in saline with 0.5% bovine serum albumin, 0.1 ml/kg) every 10 minutes consecutively three times or until the increase in arterial pressure produced was within 3 mm Hg for two consecutive injections. The last two AII injections are averaged and are referred to as the control response to AII. Ten minutes after the final control AII injection, the test compound (dissolved in an aqueous or partial aqueous/partial polyethylene glycol solution) was administered iv at a dose of 3-100 mg/kg in approximately 0.2 ml of the solution. AII injections were then given 1, 5, 10, 20, 30, 45, 60, 75, 90, and 120 minutes after administration of the test compound and the response of arterial pressure monitored. The response to AII was reported as percent of the control response (the lower the percent the greater the inhibition of the AII pressor response). Only one compound at one dose could be tested in each rat. Each compound was tested in at least two rats and the values for the two rats averaged. The results for antagonism of the AII pressor response are reported as maximal inhibition (100 percent of control response at the point of maximal inhibition) and duration of inhibition (time from maximal inhibition to time the response has recovered to 50% of the control).

Time control animals are treated in a manner identical to that described above except that they receive 0.2 ml saline instead of a test compound.

Intraduodenal Administration

Compounds were tested for absorption from the gastrointestinal tract following intraduodenal administration. The protocol was the same as that for the intravenous screening assay with the following exceptions: a small catheter was placed in the duodenum through a small midline incision posterior to the sternum. The compounds for intraduodenal administration were dissolved or suspended in an aqueous solution and administered in a volume of 0.4-0.5 ml through the duodenal catheter at a dose of 10-300 mg/kg. The response to AII was tested at the same time points following administration of the test compound except that the 1 minute reading was eliminated. The results for intraduodenal administration of the test compound are shown in Table 2. Angiotensin II was, therefore, given at a higher dose of 100 µg/kg to produce a consistent arterial pressure response. The results are presented in the same manner as for the intravenous dosing. Time control animals receiving 0.4-0.5 ml of saline into the duodenum instead of the test compound are also performed. Results are reported in Table II.

TABLE II

| Ex. # | IC$_{50}$ µM | pA$_2$ | I.V. | I.D. |
|---|---|---|---|---|
| In Vivo and In Vitro Angiotensin II Activity of Compounds of the Invention ||||| 
| 1 | 0.8 250 | 6.0 | 72% @ 30 mg | 72% @ 100 mg |
| 2 | 0.5 140 | 6.6 | 100% @ 10 mg | NA |
| 3 | 1.4 24 | 5.9 | — | — |
| 4 | 2.3 550 | 6.0 | — | — |
| 5 | 1.4 349 | 5.9 | — | — |
| 6 | 2.5 230 | 5.1 | — | — |
| 7 | 0.8 117 | 6.5 | — | — |
| BIO DATA |||||
| 10 | 2 161 | 5.6 | | |
| 11 | 7.1 7.1 | 6.4 | | |
| 12 | 4.0 390 | 6.8 | | |
| 13 | 1.9 38 | 5.5 | | |
| 14 | 2.3 108 | 6.1 | | |
| 20 | 0.71 324 | | | |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A Compound of Formula III:

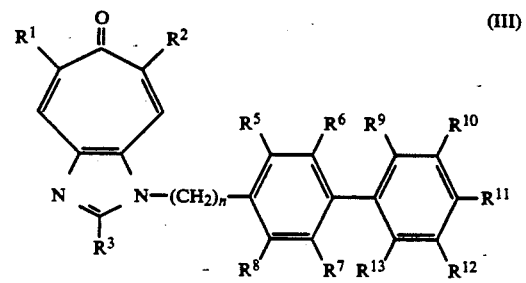

wherein n is a number selected from one to three, inclusive; wherein each of $R^1$ and $R^2$ is independently selected from hydrido, linear or branched alkyl, linear or branched alkenyl, linear or branched alkynyl, cycloalkyl, cycloalkenyl, cycloalkylalkyl, cycloalkenylalkyl, aryl, aralkyl, alkylaryl, halo, nitro, cyano, hydroxyl, alkoxy, alkoxyalkyl, aryloxy, alkylthio, alkylsulfinyl, alkylsulphonyl, arylthio, arylsulfinyl, arylsulphonyl and carboxylic acid radicals of the formula

wherein $T^1$ can be hydrido, linear or branched alkyl, linear or branched alkenyl, linear or branched alkynyl, cycloalkyl, cycloalkenyl, cycloalkylalkyl and cycloalkenylalkyl; wherein each of $R^1$ and $R^2$ can be further independently selected from carbonyl radicals of the formula

wherein $T^2$ can be hydrido, linear or branched alkyl, linear or branched alkenyl, linear or branched alkynyl, cycloalkyl, cycloalkenyl, cycloalkylalkyl and cycloalkenylalkyl; and wherein each of $R^1$ and $R^2$ can be further independently selected from a carboxamido radicals of the formula

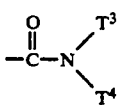

wherein each of $T^3$ and $T^4$ is independently selected from hydrido, linear or branched alkyl, linear or branched alkenyl, linear or branched alkynyl, cycloalkyl, cycloalkenyl, cycloalkylalkyl and cycloalkenylalkyl; wherein $R^1$ and $R^2$ can be an amino group of the

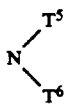

wherein each of $T^5$ and $T^6$ is independently selected from hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

2. Compound of claim 1 wherein n is a number selected from one to three, inclusive; wherein each of $R^1$ and $R^2$ is independently selected from hydrido, linear or branched alkyl, linear or branched alkenyl, linear or branched alkynyl, alkoxyalkyl, cycloalkyl, cycloalkenyl, cycloalkylalkyl, cycloalkenylalkyl, aryl, aralkyl and alkylaryl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

3. Compound of claim 1 wherein n is a number selected from one to three, inclusive; wherein each of $R^1$ and $R^2$ is independently selected from hydrido, halo, nitro, cyano, hydroxyl, alkoxy, alkoxyalkyl, aryloxy, alkylthio, alkylsulfinyl, alkylsulphonyl, arylthio, arylsulfinyl and arylsulphonyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

4. Compound of claim 41 wherein n is a number selected from one to three, inclusive; wherein each of $R^1$ and $R^2$ is independently selected from hydrido and carboxylic acid radical the formula

wherein $T^1$ can be hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

5. Compound of claim 1 wherein n is a number selected from one to three, inclusive; wherein each of $R^1$ and $R^2$ can be independently selected from hydrido and carbonyl radicals of the formula

wherein $T^2$ can be hydrido, linear or branched alkyl, linear or branched alkenyl, linear or branched alkynyl, alkoxyalkyl, cycloalkyl, cycloalkenyl, cycloalkylalkyl and cycloalkenylalkyl; wherein $R^3$ is selected from linear or branched alkyl, alkenyl, alkynyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

6. Compound of claim 1 wherein n is a number selected from one to three, inclusive; wherein each of $R^1$ and $R^2$ can be independently selected from hydrido and carboxamido radicals of the formula

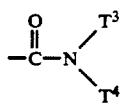

wherein each of $T^3$ and $T^4$ is independently selected from hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

7. Compound of claim 1 wherein n is a number selected from one to three, inclusive; wherein each of $R^1$ and $R^2$ may be independently selected from hydrido and an amino groups of the formula

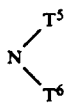

wherein each of $T^5$ and $T^6$ is independently selected from hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

8. A pharmaceutical composition comprising a therapeutically-effective amount of an angiotensin II antagonist compound and a pharmaceutically-acceptable carrier or diluent, said antagonist compound selected from a family of compounds of Formula III:

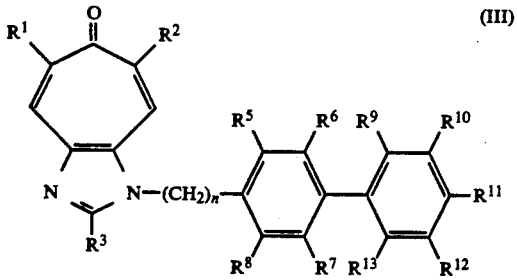

(III)

wherein n is a number selected from one to three, inclusive; wherein each of $R^1$ and $R^2$ is independently selected from hydrido, linear or branched alkyl, linear or branched alkenyl, linear or branched alkynyl, cycloalkyl, cycloalkenyl, cycloalkylalkyl, cycloalkenylalkyl, aryl, aralkyl, alkylaryl, halo, nitro, cyano, hydroxyl, alkoxy, alkoxyalkyl, aryloxy, alkylthio, alkylsulfinyl, alkylsulphonyl, arylthio, arylsulfinyl, arylsulphonyl and carboxylic acid radicals of the formula

wherein $T^1$ can be hydrido, linear or branched alkyl, linear or branched alkenyl, linear or branched alkynyl, cycloalkyl, cycloalkenyl, cycloalkylalkyl and cycloalkenylalkyl; wherein each of $R^1$ and $R^2$ can be further independently selected from carbonyl radicals of the formula

wherein $T^2$ can be hydrido, linear or branched alkyl, linear or branched alkenyl, linear or branched alkynyl, cycloalkyl, cycloalkenyl, cycloalkylalkyl and cycloalkenylalkyl; and wherein each of $R^1$ and $R^2$ can be further independently selected from a carboxamido radicals of the formula

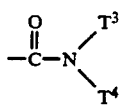

wherein each of $T^3$ and $T^4$ is independently selected from hydrido, linear or branched alkyl, linear or branched alkenyl, linear or branched alkynyl, cycloalkyl, cycloalkenyl, cycloalkylalkyl and cycloalkenylalkyl; wherein $R^1$ and $R^2$ can be an amino group of the formula

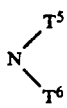

wherein each of $T^5$ and $T^6$ is independently selected from hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

9. The composition of claim 8 wherein n is a number selected from one to three, inclusive; wherein each of $R^1$ and $R^2$ is independently selected from hydrido, linear or branched alkyl, linear or branched alkenyl, linear or branched alkynyl, alkoxyalkyl, cycloalkyl, cycloalkenyl, cycloalkylalkyl, cycloalkenylalkyl, aryl, aralkyl and alkylaryl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

10. The composition of claim 8 wherein n is a number selected from one to three, inclusive; wherein each of $R^1$ and $R^2$ is independently selected from hydrido, halo, nitro, cyano, hydroxyl, alkoxy, alkoxylakyl, aryloxy, alkylthio, alkylsulfinyl, alkylsulphonyl, arylthio, arylsulfinyl and arylsulphonyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

11. The composition of claim 8 wherein n is a number selected from one to three, inclusive; wherein each of $R^1$ and $R^2$ is independently selected from hydrido and carboxylic acid radical the formula

wherein $T^1$ can be hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

12. The composition of claim 8 wherein n is a number selected from one to three, inclusive; wherein each of $R^1$ and $R^2$ can be independently selected from hydrido and carbonyl radicals of the formula

wherein $T^2$ can be hydrido, linear or branched alkyl, linear or branched alkenyl, linear or branched alkynyl, alkoxyalkyl, cycloalkyl, cycloalkenyl, cycloalkylalkyl and cycloalkenylalkyl; wherein $R^3$ is selected from linear or branched alkyl, alkenyl, alkynyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

13. The composition of claim 8 wherein n is a number selected from one to three, inclusive; wherein each of $R^1$ and $R^2$ can be independently selected from hydrido and carboxamido radicals of the formula

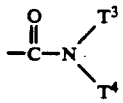

wherein each of $T^3$ and $T^4$ is independently selected from hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

14. The composition of claim 8 wherein n is a number selected from one to three, inclusive; wherein each of $R^1$ and $R^2$ may be independently selected from hydrido and an amino groups of the formula

wherein each of $T^5$ and $T^6$ is independently selected from hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

15. A therapeutic method for treating hypertension, said method comprising administering to a hypertensive patient a therapeutically-effective amount of an angiotensin II antagonist compound of Formula III:

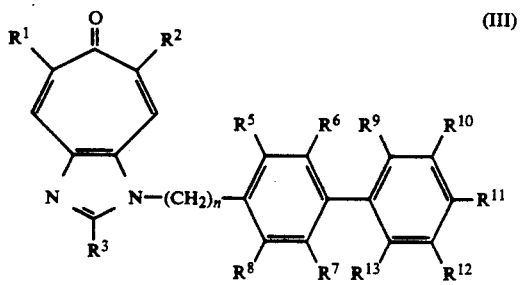

(III)

wherein n is a number selected from one to three, inclusive; wherein each of $R^1$ and $R^2$ is independently selected from hydrido, linear or branched alkyl, linear or branched alkenyl, linear or branched alkynyl, cycloalkyl, cycloalkenyl, cycloalkylalkyl, cycloalkenylalkyl, aryl, aralkyl, alkylaryl, halo, nitro, cyano, hydroxyl, alkoxy, alkoxyalkyl, aryloxy, alkylthio, alkylsulfinyl, alkylsulphonyl, arylthio, arylsulfinyl, arylsulphonyl and carboxylic acid radicals of the formula

wherein $T^1$ can be hydrido, linear or branched alkyl, linear or branched alkenyl, linear or branched alkynyl, cycloalkyl, cycloalkenyl, cycloalkylalkyl and cycloalkenylalkyl; wherein each of $R^1$ and $R^2$ can be further independently selected from carbonyl radicals of the formula

wherein $T^2$ can be hydrido, linear or branched alkyl, linear or branched alkenyl, linear or branched alkynyl, cycloalkyl, cycloalkenyl, cycloalkylalkyl and cycloalkenylalkyl; and wherein each of $R^1$ and $R^2$ can be further independently selected from a carboxamido radicals of the formula

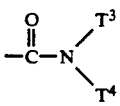

wherein each of $T^3$ and $T^4$ is independently selected from hydrido, linear or branched alkyl, linear or branched alkenyl, linear or branched alkynyl, cycloalkyl, cycloalkenyl, cycloalkylalkyl and cycloalkenylalkyl; wherein $R^1$ and $R^2$ can be an amino group of the formula

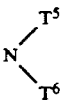

wherein each of $T^5$ and $T^6$ is independently selected from hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

16. The method of claim 15 wherein n is a number selected from one to three, inclusive; wherein each of $R^1$ and $R^2$ is independently selected from hydrido, linear or branched alkyl, linear or branched alkenyl, linear or branched alkynyl, alkoxyalkyl, cycloalkyl, cycloalkenyl, cycloalkylalkyl, cycloalkenylalkyl, aryl, aralkyl and alkylaryl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

17. The method of claim 15 wherein n is a number selected from one to three, inclusive; wherein each of $R^1$ and $R^2$ is independently selected from hydrido, halo, nitro, cyano, hydroxyl, alkoxy, alkoxylalkyl, aryloxy, alkylthio, alkylsulfinyl, alkylsulphonyl, arylthio, arylsulfinyl and arylsulphonyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

18. The method of claim 15 wherein n is a number selected from one to three, inclusive; wherein each of $R^1$ and $R^2$ is independently selected from hydrido and carboxylic acid radical the formula

wherein $T^1$ can be hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, alkoxyalkyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

19. The method of claim 15 wherein n is a number selected from one to three, inclusive; wherein each of $R^1$ and $R^2$ can be independently selected from hydrido and carbonyl radicals of the formula

wherein $T^2$ can be hydrido, linear or branched alkyl, linear or branched alkenyl, linear or branched alkynyl, alkoxyalkyl, cycloalkyl, cycloalkenyl, cycloalkylalkyl and cycloalkenylalkyl; wherein $R^3$ is selected from linear or branched alkyl, alkenyl, alkynyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

20. The method of claim 15 wherein n is a number selected from one to three, inclusive; wherein each of $R^1$ and $R^2$ can be independently selected from hydrido and carboxamido radicals of the formula

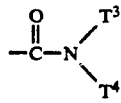

wherein each of $T^3$ and $T^4$ is independently selected from hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

21. The method of claim 15 wherein n is a number selected from one to three, inclusive; wherein each of $R^1$ and $R^2$ may be independently selected from hydrido and an amino groups of the formula

wherein each of $T^5$ and $T^6$ is independently selected from hydrido, linear or branched alkyl, linear or branched alkenyl, linear or branched alkynyl, cycloalkyl, cycloalkenyl, cycloalkylalkyl and cycloalkenylalkyl; wherein $R^3$ is selected from linear or branched alkyl, alkenyl, alkynyl, cycloalkyl, cycloalkylalkyl, cycloalkenyl, cycloalkenylalkyl, arylalkyl and alkylcycloalkylalkyl; wherein one of $R^5$ through $R^{13}$ is selected from tetrazolyl and COOY wherein Y is selected from hydrido and alkyl; and wherein each of the remaining $R^5$ through $R^{13}$ is hydrido; or a pharmaceutically-acceptable salt thereof.

* * * * *